US008778986B1

(12) United States Patent
Tan et al.

(10) Patent No.: US 8,778,986 B1
(45) Date of Patent: Jul. 15, 2014

(54) TREATMENT OF GLYCOGEN SYNTHASE KINASE-BASED DISEASE

(75) Inventors: Jun Tan, Tampa, FL (US); Doug Shytle, Lutz, FL (US); Kavon Rezai-Zadeh, Tampa, FL (US)

(73) Assignee: University of South Florida, Tampa, FL (US)

( * ) Notice: Subject to any disclaimer, the term of this patent is extended or adjusted under 35 U.S.C. 154(b) by 464 days.

(21) Appl. No.: 12/020,214

(22) Filed: Jan. 25, 2008

Related U.S. Application Data

(60) Provisional application No. 60/886,573, filed on Jan. 25, 2007.

(51) Int. Cl.
*C07D 311/30* (2006.01)
*A61K 31/352* (2006.01)

(52) U.S. Cl.
CPC ............ *C07D 311/30* (2013.01); *A61K 31/352* (2013.01)
USPC .......................................... 514/456; 549/403

(58) Field of Classification Search
None
See application file for complete search history.

(56) References Cited

U.S. PATENT DOCUMENTS

| 6,451,837 | B1 * | 9/2002 | Baskys ........................... | 514/411 |
| 6,719,520 | B2 * | 4/2004 | Coghlan et al. ................ | 514/425 |
| 7,053,116 | B2 * | 5/2006 | Schubert et al. .............. | 514/452 |
| 8,574,633 | B2 * | 11/2013 | Xie et al. ...................... | 424/725 |
| 2001/0047032 | A1 * | 11/2001 | Castillo et al. ................ | 514/453 |
| 2003/0055103 | A1 * | 3/2003 | Heinzen et al. ............... | 514/456 |
| 2006/0025337 | A1 * | 2/2006 | Sinclair et al. ................. | 514/12 |

FOREIGN PATENT DOCUMENTS

| WO | WO01/49281 A2 | * | 7/2001 | |
| WO | WO2006/076681 | * | 7/2006 | |
| WO | WO2007/005879 | * | 1/2007 | |
| WO | WO2007/008548 | * | 1/2007 | ............. A61K 31/05 |

OTHER PUBLICATIONS (R) Commenges et al., "Intake of Flavonoids and Risk of Dementia," European Journal of Epidemiology, 16(4), 357-363 (Apr. 2000).*
(S) de Rijk et al., "Dietary Antioxidants and Parkinson's Disease," Archives of Neurology, 54(6), 762-765 (Jun. 1997); only abstract supplied.*
(T) Orgogozo et al., "Wine Consumption and Dementia in the Elderly: A Prospective Community Study in the Bordeaux Area," Revue Neurologique, 153(30), 185-192 (Apr. 1997): only abstract supplied.*
(U) Hertog et al. (I), "Content of Potentially Anticarcinogenic Flavonoids of Tea Infusions," Journal Agricultural & Food Chem., 41(8), 1242-1246 (Aug. 1993).*
(V) Hertog et al. (II), "Optimization of Quantitative HPLC Determination of Potentially Anticarcinogenic Flavonoids in Vegetables and Fruits," Journal Agricultural & Food Chem., 40(9), 1591-1598 (Sep. 1992).*
(W) Hertog et al. (III), "Content of Potentially Anticarcinogenic Flavonoids of 28 Vegetables and 9 Fruits Commonly Consumed in The Netherlands," Journal Agricultural & Food Chem., 40(12), 2379-2383 (Dec. 1992).*
Oken et al., "The Efficacy of Ginkgo Biloba on Cognitive Function in Alzheimer Disease" Archives of Neurology (1998) vol. 55 pp. 1409-1415.*
Chemical Abstracts Registry entry 264218-23-7, "SB 415286" entered into registry May 10, 2000.*
Ramassamy, C. 2006. "Emerging role of polyphenolic compounds in the treatment of neurodegenerative diseases: A review of their intracellular targets." European Journal of Pharmacology. 2006. 545(1). pp. 51-64. General review of polyphenols and neurodegenerative diseases.
Hooper, Lee., Cassidy, Aedin. 2006. "A review of the health care potential of bioactive compounds." Journal of the Science of Food and Agriculture. 2006. 86(12). pp. 1805-1813. Mentions Diabetes and Luteolin. Reviews other bioactive compounds, Only Abstract supplied.
Zareba, G., Serradell, N., Castner, R., Davies, S. L., Prous, J., Mealy, N. 2005. "Drugs of the Future." 2005. 30(12). pp. 1253-1282. Phytotherapies for diabetes. Involves Luteolin, Only abstract supplied,.
Song, Y. Q., Manson, J. E., Buring, J. E., Sesso, H. D., Liu, S. M. 2005. "Associations of dietary flavonoids with risk of type 2 diabetes, and markers of insulin resistance and systemic inflammation in women: a prospective study and cross-sectional analysis." Journal of the American College of Nutrition. 2005. 24(5). pp. 376-384, Only absract supplied.
Vertommen, J., Engelen, W., De Leeuw, I. 1996. "Skin blood cell flux in IDDM before and after treatment with diosmin." International Journal of Microcirculation Clinical and Experimental. 1996. 16(4). pp. 214, Only bibliographic data supplied.
Anonymous, Monograph. Diosmin,Altern Med Rev. 2004. 9(3). pp. 308-311.
Vertommen, J., Enden, M. Van Den, Simoens, L., Leeuw, 1.1994. "De Flavonoid diosmin treatment reduces glycation of proteins and lipid peroxidation in experimental diabetic rats." Phytotherapy Research. 1994. 8(7). pp. 430-432, Only abstract supplied.
Funamoto, S., Morishima-Kawashima, M., Tanimura, Y., Hirotani, N., Saido, T.C., et al. 2004. "Truncated carboxyl-terminal fragments of beta-amyloid precursor protein are processed to amyloid beta-proteins 40 and 42." Biochemistry. 2004. 43. pp. 13532-13540.

(Continued)

*Primary Examiner* — Eric S Olson
(74) *Attorney, Agent, or Firm* — Robert J. Varkonyi; Smith & Hopen, P.A.

(57) ABSTRACT

The bioflavonoid luteolin reduces amyloid-β peptide (Aβ) generation. Luteolin is also a selective GSK-3 inhibitor that 1) decreases amyloidogenic γ-secretase APP processing, and 2) promotes presenilin-1 (PS1) carboxyl-terminal fragment (CTF) phosphorylation. GSK-3α activity is essential for both PS1 CTF phosphorylation states and PS1-APP interaction. To validate The findings were validated in vivo, using a Tg2576 Alzheimer's Disease model system. Luteolin treatment decreased soluble Aβ levels, reduced GSK-3 activity, and disrupted PS1-APP association.

4 Claims, 27 Drawing Sheets

(56) References Cited

OTHER PUBLICATIONS

Sambamurti, K., Greig, N.H., Lahiri, D.K. 2002. "Advances in the cellular and molecular biology of the beta-amyloid protein in Alzheimer's disease." Neuromolecular Med. 2002. 1. pp. 1-31, Only abstract supplied.

Golde, T.E., Eckman, C.B., Younkin, S.G., 2000. "Biochemical detection of Abeta isoforms: implications for pathogenesis, diagnosis, and treatment of Alzheimer's disease." Biochim Biophys Acta. 2000. 1502. pp. 172-187.

Huse, J.T., Doms, R.W. 2000. "Closing in on the amyloid cascade: recent insights into the cell biology of Alzheimer's disease." Mol Neurobiol. 2000. 22. pp. 81-98.

Selkoe, D.L., Yamazaki, T., Citron, M., Podlisny, M.B., Koo, E.H., et al. 1996. "The role of APP processing and trafficking pathways in the formation of amyloid beta-protein." Ann, NY. Acad Sci. 1996. 777. pp. 57-64, Only abstract supplied.

Loo, D.T., Copani, A., Pike, C.J., Whittemore, E.R., Walencewicz, A.J., et al. 1993. "Apoptosis is induced by beta-amyloid in cultured central nervous system neurons." Proc Natl Acad Sci. USA. 1993. 90. pp. 7951-7955.

Bradt, B.M., Kolb, W.P., Cooper, N.R. 1998. "Complement-dependent proinflammatory properties of the Alzheimer's disease beta-peptide." J Exp Med. 1998. 188. pp. 431-438.

Suo, Z., Tan, J., Placzek, A., Crawford, F., Fang, C., et al. 1998. "Alzheimer's beta-amyloid peptides induce inflammatory cascade in human vascular cells: the roles of cytokines and CD40." Brain Res. 1998. 807. pp. 110-117.

Murakami, K., Irie, K., Ohigashi, H., Hara, H., Nagao, M., et al. 2005. "Formation and stabilization model of the 42-mer Abeta radical: implications for the long-lasting oxidative stress in Alzheimer's disease." J Am Chem Soc. 2005. 127. pp. 15168-15174.

Hensley, K., Carney, J.M., Mattson, M.P., Aksenova, M., Harris, M., et al. 1994. "A model for beta-amyloid aggregation and neurotoxicity based on free radical generation by the peptide: relevance to Alzheimer disease." Proc Natl Acad Sci. USA. 1994. 91. pp. 3270-3274.

Schenk, D.B., Rydel, R.E., May, P., Little, S., Panetta, J., et al. 1995. "Therapeutic approaches related to amyloid-beta peptide and Alzheimer's disease." J Med Chem. 1995. 38. pp. 4141-4154.

Sinha, S., Lieberburg, I. 1999. "Cellular mechanisms of beta-amyloid production and secretion." Proc Natl Acad Sci. USA. 1999. 96. pp. 11049-11053.

Vassar, R., Bennett, B.D., Babu-Khan, S., Kahn, S., Mendiaz, E.A., et al. 1999. "Beta-Secretase Cleavage of Alzheimer's Amyloid Precursor Protein by the Transmembrane Aspartic Protease BACE." Science. 1999. 286. pp. 735-741.

Yan, R., Bienkowski, M.J., Shuck, M.E, Miao, H., Tory, M.C., Pauley, A.M., et al. 1999. "Membrane-anchored aspartyl protease with Alzheimer's disease beta-secretase activity." Nature. 1999. 402. pp. 533-537.

Steiner, H., Duff, K, Capell, A., Romig, H., Grim, M.G., et al. 1999. "A loss of function mutation of presenilin-2 interferes with amyloid beta-peptide production and notch signaling." J Biol Chem. 1999. 274. pp. 28669-28673.

De Strooper, B., Saftig, P., Craessaerts, K., Vanderstichele, H., Guhde, G., et al. 1998. "Deficiency of presenilin-1 inhibits the normal cleavage of amyloid precursor protein." Nature. 1998. 391. pp. 387-390.

Citron, M., Diehl, T.S., Gordon, G., Biere, A.L., Seubert, P., et al. 1996. "Evidence that the 42- and 40-amino acid forms of amyloid beta protein are generated from the beta-amyloid precursor protein by different protease activities." Proc Natl Acad Sci. USA. 1996. 93. pp. 13170-13175.

Evin, G., Cappai, R., Li, Q.X., Culvenor, J.G., Small, D.H., et al. "Candidate gamma-secretases in the generation of the carboxyl terminus of the Alzheimer's disease beta A4 amyloid: possible involvement of cathepsin D." Biochemistry. 1995. 34. pp. 14185-14192.

Barten, D.M., Meredith, J.E. Jr., Zaczek, R., Houston, J.G., Albright, C.F. 2006. "Gamma-secretase inhibitors for Alzheimer's disease: balancing efficacy and toxicity." Drugs R D. 2006. 7. pp. 87-97, Only abstract supplied.

Evin, G., Sernee, M.F., Masters, C.L. 2006. "Inhibition of gamma-secretase as a therapeutic intervention for Alzheimer's disease: prospects, limitations and strategies." CNS Drugs. 2006. 20. pp. 351-372.

Dovey, H.F., John, V., Anderson, J.P., Chen, L.Z., De Saint, Andrieu P., Fang, L.Y., et al. 2001. "Functional gamma-secretase inhibitors reduce beta-amyloid peptide levels in brain." J Neurochem. 2001. 76. pp. 173-181, Only abstract supplied.

Citron, M., Diehl, T.S., Capell, A., Haass, C., Teplow, D.B., et al. 1996. "Inhibition of amyloid beta-protein production in neural cells by the serine protease inhibitor AEBSF." Neuron. 1996. 17. pp. 171-179.

Games, D., Adams, D., Alessandrini, R., Barbour, R., Berthelette, P., et al. 1995, "Alzheimer-type neuropathology in transgenic mice over expressing V717F beta-amyloid precursor protein." Nature. 1995. 373. pp. 523-527.

Higaki, L., Quon, D., Zhong, Z., Cordell,I B. 1995. "Inhibition of beta-amyloid formation identifies proteolytic precursors and subcellular site of catabolism." Neuron. 1995. 14. pp. 651-659.

Klafki, H.W., Paganetti, P.A., Sommer, B., Staufenbiel, M. 1995. "Calpain inhibitor I decreases beta A4 secretion from human embryonal kidney cells expressing beta-amyloid precursor protein carrying the APP670/671 double mutation." Neurosci. Lett. 1995. 201. pp. 29-32.

Comery, T.A., Martone, R.L., Aschnies, S., Atchison, K.P., Diamantidis, G., et al. 2005. "Acute gamma-secretase inhibition improves contextual fear conditioning in the Tg2576 mouse model of Alzheimer's disease." J Neurosci. 2005. 25. pp. 8898-8902.

Engel, T., Hernandez, F., Avila, J., Lucas, J.J. 2006. "Full reversal of Alzheimer's disease-like phenotype in a mouse model with conditional overexpression of glycogen synthase kinase-3." J Neurosci. 2006 .26. pp. 5083-5090.

Kozlovsky, N., Belmaker, R.H., Agam, G. 2000. "Low GSK-3beta immunoreactivity in postmortem frontal cortex of schizophrenic patients." Am. J Psychiatry. 2000. 157. pp. 831-833.

Carmichael, J., Sugars, K.L., Bao, Y.P., Rubinsztein, D.C. 2002. "Glycogen synthase kinase-3beta inhibitors prevent cellular polyglutamine toxicity caused by the Huntington's disease mutation." J Biol Chem. 2002. 277. pp. 33791-33798.

Agam, G., Levine, J. 1998. "Glycogen synthase kinase-3—a new target for lithium's effects in bipolar patients?" Human Psychopharmacology Clinical and Experimental. 1998. 13. pp. 463-465.

Ishiguro, K., Shiratsuchi, A. Sato, S., Omori, A., Arioka, M., et al. "Glycogen synthase kniase 3B is identical to tau protein kinase I generating several epitopes of paired helical filaments." FEBS Lett. 1993. 25. pp. 167-172, Only bibliographic data supplied.

Aplin, A.E. Gibb, G.M., Jacobsen, J.S., Gallo, J.M., Anderton, B.H. 1996. "In vito phosphorylation of the cytoplasmic domain of the amyloid precursor protein by glycogen synthase kinase-3B." J. Neurochem. 1996.67. pp. 699-707.

Takashima, A., Noguchi, K., Michel, G., Mercken, M., Hishi, M., et al. 1996. "Exposure of rat hippocampal neurons to amyloid B peptide (25-35) induces the inactivation of phosphatidylinositol-3 kinase and the activation of tau protein kinase 1/glycogen synthase kinase-3B." Neurosci. Lett. 1996. pp. 33-36.

Takashima, A., Honda, T., Yasutake, K., Michel, G., Murayama, O., et al. 1998. "Activation of tau protein kinase 1/glycogen synthase-3B by amyloid peptide (25-35) enhances phosphorylation of tau in hippocampel neurons." Neurosci Res. 1998. 32. pp. 317-323.

Takashima, A., Murayama, M., Murayama, O., Kohno, T., Hinda, T., et al. 1998. "Presenilin 1 associates with glycogen synthase kinase-3B and its sustrate tau." Proc Natl Acad Sci. USA. 1998. 95. pp. 9637-9641.

Phiel, C.J., Wilson, C.A., Lee, V.M., Klein, P.S. 2003. "GSK-3alpha regulates production of Alzheimer's disease amyloid-beta peptides." Nature. 2003. 423. pp. 435-439.

Barberger-Gateau, P., Raffaitin, C., Letenneur, L., Berr, C., Tzourio, C., et al. 2007. "Dietary patterns and risk of dementia: the Three-City cogort study." Neurology. 2007. 69. pp. 1921-1930.

(56) References Cited

OTHER PUBLICATIONS

Dai, Q., Borenstein, A.R., Wu, Y., Jackson, J.C., Larson, E.B. 2006. "Fruit and vegetable juices and Alzheimer's disease: the Kame Project." Am. J Med. 2006. 119. pp. 751-759.
Marambaud, P., Zhao, H., Davies, P. 2005. " Resveratrol promotes clearance of Alzheimer's disease amyloid-beta peptides." J Biol Chem. 2005. 280. pp. 37377-37382.
Rezai-Zadeh, K., Shytle, D., Sun, N., Mori, T., Hou, H., et al. 2005. "Green tea epigallocatechin-3-gallate (EGCG) modulates amyloid precursor protein cleavage and reduces cerebral amyloidosis in Alzheimer transgenic mice." J Neurosci. 2005. 25. pp. 8807-8814.
Yang, F., Lim, G.P., Begum, A.N., Ubeda, O.J., Simmons, M.R., et al. 2005. "Curcumin inhibits formation pf amyloid betaoligomers and fibrils, binds plaques, and reduces amyloid in vivo." J Biol Chem. 2005. 280. pp. 5892-5901.
Hsiao, K., Chapman, P., Nilsen, S., Eckman, C., Harigaya, Y., et al. 1996. Correlative memory deficits, a elevation, and amyloid plaques in transgenic mice. Science. 1996. 274. pp. 99-102, Only abstract supplied.
Tan, J., Town, T., Crawford, F., Mori, T., Delledonne, A., et al. 2002. "Role of CD40 ligand in amyloidosis in transgenic Alzheimer's mice." Nat Neurosci. 2002. 5. pp. 1288-1293.
Wittemer, S.M., Ploch, M., Windeck, T., Muller, S.C., Drewelow, B., et al. "Bioavailability and pharmacokinetics of caffeoylquinic acids and flavonoids after oral administration of Artichoke leaf extracts in humans." Phytomedicine. 2005. 12. pp. 28-38.
Shimoi, K., Okada, H., Furugori, M., Goda, T., Takase, S., et al. "Intestinal absorption of luteolin and luteolin 7-O-beta-glucoside in rats and humans." FEBS. Lett. 1998. 438. pp. 220-224.
Cova, D., De Angelis, L., Giavarini, F., Palladini, G., Perego, R. 1992. "Pharmacokinetics and metabolism of oral diosmin in healthy volunteers." Int J Clin Pharmacol Ther Toxicol. 1992. 30. pp. 29-33, Only abstract supplied.
Hong, M., Chen, D.C., Klein, P.S., Lee, V.M. 1997. "Lithium reduces tau phosphorylation by inhibition of glycogen synthase kinase-3." J Biol Chem. 1997. 272. pp. 25326-25332.
Munoz-Montano, J.R., Moreno, F.J., Avila, J., Diaz-Nido, J. 1997. "Lithium inhibits Alzheimer's disease-like tau protein phosphorylation in neurons." FEBS. Lett. 1997. 411. pp. 183-188.
Shah, S., Lee, S.F., Tabuchi, K., Hao, Y.H., Yu, C., et al. 2005. "Nicastrin functions as a gamma-secretase-substrate receptor." Cell. 2005. 122. pp. 435-447.
Seeger, M., Nordstedt, C., Petanceska, S., Kovacs, D.M., Gouras, G.K., et al. 1997. "Evidence for phosphorylation and oligomeric assembly of presenilin 1." Proc Nati Acad Sci. USA. 1997. 94. pp. 5090-5094.
Walter, J., Grunberg, J., Capell, A., Pesold, B., Sschindzielorz, A., et al. 1997. "Proteolytic processing of the Alzheimer disease-associated presenilin-1 generates an in vivo substrate for protein kinase C." Proc Natl Acad Sci. USA. 1997. 94. pp. 5349-5354.
Buxbaum, J.D., Gandy, S.E., Cisshetti, P., Ehrlich, M.E., Czernik, A.J., et al. 1990. "Processing of Alzheimer beta/A4 amyloid precursor protein: modulation by agents that regulate protein phosphorylation." Proc Natl Acad Sci. USA. 1990. 87. pp. 6003-6006.
Lopez-Perez, E., Zhang, Y., Ffrank, S.J., Creemers, J., Seidah, N., et al. 2001. "Constitutive alpha-secretase cleavage of the beta-amyloid precursor protein in the furin-deficient LoVo cell line: involvement of the pro-hormone convertase 7 and the disintegrin metalloprotease ADAM10." J Neurochem. 2001. 76. pp. 1532-1539.
Buxbaum, J. D., Liu, K. N., Luo, Y., Slack, J. L., Stocking, K. L., et al. 1998. "Evidence that tumor necrosis factor a converting enzyme is involved in regulated a-secretase cleavage of the Alzheimer amyloid protein precursor." J Biol Chem. 1998. 273. pp. 27765-27767.

Savage, M., Trusko, S. P., Howland, D. S., Pinsker, L. R., Mistreta, S., et al. 1998. "Turnover of amyloid B-protein in mouse brain and acute reduction of its level by phorbal ester." J Neurosci. 1998. 18. pp. 1743-1752.
Hung, A. Y., Haass, C., Nitschm R. M., Qiu, W. Q., Citron, M., et al. 1993. "Activation of protein kinase C inhibits cellular production of the amyloid beta-protein." J Biol Chem. 1993. 268. pp. 22959-22962.
Horvathova, K., Novotny, L., Tothova, D., Vachalkove, A. 2004. "Determination of free radical scavenging activity of quercetin, rutin, luteolin and apigenin in H202-treated human ML cells K562." Neoplasma. 2004. 51. pp. 395-399, Only abstract supplied.
Hougee, S., Sanders, A., Faber, J., Graus, Y. M., Van Den Berg, W. B., et al. 2005. "Decreased pro-inflammatory cytokine production by LPS-stimulated PBMC upon in vitro incubation with the flavonoids apigenin, luteolin or chrysin, due to selective elimination of monocytes/macrophages." Biochem Pharmacol. 2005. 69. pp. 241-248.
Verbeek, R., Plomp, A. C., Van Tol, E. A., Van Noort, J. M. 2004. "The flavones luteolin and apigenin inhibit in vitro antigen-specific proliferation and interferon-gamma production by murine and human autoimmune T cells." Biochem Pharmacol. 2004. 68. pp. 621-629.
Hirano, T., Higa, S., Arimitsu, J., Naka, T., Ogata, A., et al. 2006. "Luteolin, a flavonoid, inhibits AP-1 activation by basophils." Biochem Biophys Res Commun. 2006. 340. pp. 1-7.
Hirano, T., Higa, S., Arimitsu, J., Naka, T., Shimas, Y., et al. 2004. "Flavonoids such as luteolin, fisetin and apigenin are inhibitors of interleukin-4 and interleukin-13 production by activated human basophils." Int Arch Allergy Immunol. 2004. 134. pp. 135-140, Only abstract supplied.
University of Leeds. 2011. "Unfolding amyloid secrets." ScienceDaily. Retrieved Jun. 20, 2011, from http://www.sciencedaily.com/releases/2011/01/110120124953.htm.
Wikipedia. 2011. "Amyloid." Wikimedia Foundation, Inc. Accessed on Jun. 20, 2011 at http://en.wikipedia.org/wiki/Amyloid.
Doble et al. 2003. "GSK-3: Tricks of the Trade for a Multi-Tasking Kinase." Journal of Cell Science. vol. 116. pp. 1175-1186.
Engel et al. 2006. "Full Reversal of Alzheimer's Disease-Like Phnotype in a Mouse Model with Conditional Overexpression of Glycogen Synthase Kinase-3." The Journal of Neuroscience. vol. 26. No. 19. pp. 5083-5090.
Farina et al. 2009. "Post-Transcriptional Regulation of Cadherin-11 Expression by GSK-3 and Beta-Catenin in Prostate and Breast Cancer Cells." PLoS One. vol. 4. Issue 3. pp. 1-9.
Lei et al. 2011. "GSK-3 in Neurodegenerative Diseases." International Journal of Alzheimer's Disease. vol. 2011. Art. ID 189246. pp. 1-9.
The Sakmar Lab. 2009. "Amyloid Disease." Accessed on Jun. 20, 2011 at http://www.sakmarlab.com/WhatWeDo/AmyloidDisease/.
wikipedia.org, "Amyloid", http://en.wikipedia.org/wiki/Amyloid, Accessed on Feb. 29, 2012.
Katsuya Tanabe, et al., Genetic Deficiency of Glycogen Synthase Kinase-3B Corrects Diabetes in Mouse Models of Insulin Resistance. PLOS Biology, Feb. 2008, vol. 6, Issue 2, pp. 0307-0318.
Espeseth, Amy S. et al. Enzyme Catalysts and Regulation: Compounds That Bind APP and Inhibit Ab Processing in Vitro Suggest a Novel Approach to Alzheimer Disease Therapeutics. The Journal of Biological Chemistry. Downloaded from http://www.jbc.org/ by guest on Jan. 28, 2014.
Moreno, Herman et al. Synaptic Transmission Block by Presynaptic Injection of Oligomeric Amyloid Beta. PNSA, Apr. 7, 2009, vol. 106, No. 14, 5901-5906. www.pnas.org/cgi/doi/10.1073/pnas.0900944106.

\* cited by examiner

Tg2576/PBS

20 X

Tg2576/PBS

20 X

Tg2576/Luteolin

20 X

Tg2576/Luteolin

20 X

TREATMENT OF GLYCOGEN SYNTHASE KINASE-BASED DISEASE

CROSS REFERENCE TO RELATED APPLICATION

This application claims priority to currently U.S. Provisional Patent Application No. 60/886,573, entitled "Glycogen Synthase Kinase-3/Gamma Secretase Inhibitors", filed on Jan. 25, 2007, the contents of which are herein incorporated by reference.

FIELD OF INVENTION

This invention relates to enzyme inhibitors. Specifically, the invention relates to inhibitors of amyloid peptide processing enzymes and treatments of Alzheimer's Disease.

BACKGROUND OF THE INVENTION

Alzheimer's Disease (AD) is a widespread cognitive disease characterized by neurodegeneration, agglomeration of β-Amyloid (Aβ) protein plaques around neurons and within cerebral vasculature, and neurofibrilliary tangles in the brain. Extensive studies indicate Aβ peptide generation and plaque aggregation are key pathological events in the development of AD. The studies evidence Aβ peptides are neurotoxic, as they are reported mediators of apoptosis, inflammation, and oxidative stress. For this reason, some of the earliest proposed therapeutic strategies entail the prevention or elimination of these Aβ peptides and subsequent deposits.

Aβ peptides are produced via the amyloidogenic pathway of amyloid precursor protein (APP) proteolysis, which involves the concerted effort of β and γ-secretases. Initially, β-secretase (BACE) cleaves APP, creating an Aβ-containing carboxyl-terminal fragment known as β-C-terminal fragment (β-CTF), or C99 and an amino-terminal, soluble APP-β (sAPP-β) fragment, which is released extracellularly. Intracellularly, the β-CTF fragment is then cleaved by a multiprotein γ-secretase complex, resulting in generation of the Aβ peptide and a smaller γ-CTF, also known as C57. While both cleavage events are essential to the formation of the peptide, it is the γ-secretase cleavage that determines which of the two major forms of the peptide ($A\beta_{1-40, 42}$) will be generated and, consequently, the peptide's ability to aggregate and the rate at which it is deposited. Thus, one clear potential therapeutic target for AD has been γ-secretase.

Notch signaling pathways are important in cellular development and dysregulation is linked to tumorigenesis. Intracellular γ-secretase processes Notch pathway receptors. Despite the potential toxicity involving possible disruption of Notch signaling and intracellular accumulation of β-CTFs, γ-secretase inhibition remains a viable anti-amyloidogenic strategy. Novel γ-secretase inhibitors (GSI) significantly reduce Aβ production both in vitro and in vivo, initial testing of GSIs has indicated the GSIs improve cognitive functioning in a transgenic mouse model of AD (Tg2576). These finding have functioned to further the vigorous search for potential candidate GSIs. Glycogen synthase kinase 3 (GSK-3) is a tonically active serine/threonine kinase, which has been implicated in several disorders of the CNS. With regard to AD, both isoforms of GSK-3 (α and β) have been found to directly phosphorylate tau on residues specific to hyperphosphorylated paired helical filaments (PHF), GSK-3β has been shown to phosphorylate APP and to contribute to Aβ mediated neurotoxicity, and GSK-3β has been found to phosphorylate PS1, which may act as a docking site for subsequent tau phosphorylation. Therefore, GSK-3 inhibitors are especially attractive as they may not only oppose Aβ generation but also neurofibrillary tangle (NFT) formation. Moreover, Phiel and colleagues (2003) reported that inhibition of the GSK-3α isoform may regulate γ-secretase cleavage of APP in a substrate-specific manner Accordingly, this selective inhibition of GSK-3 might provide the maximal therapeutic benefit while reducing the potential for toxic side-effects.

SUMMARY OF THE INVENTION

In one embodiment, flavonoids were found to selectively inhibit GSK-3 activity, thereby preventing PP1 and PS-1 phosphorylation and inactivating gamma secretase. Flavonoids within the flavone family, including lutoelin, disomin, and diosmetin were found to effectively inhibit GSK-3, and very effectively inhibit GSK-3α. Luteolin, was found to attenuate Aβ generation and possesses the ability to protect against the multiple arms of AD pathology. Luteolin, categorized as a citrus bioflavonoid, has been previously shown to be a potent free radical scavenger, anti-inflammatory agent, and immunomodulator. Treatment of both murine N2a cells transfected with the human "Swedish" mutant form of APP (Swe-APP N2a cells) and primary neuronal cells derived from Alzheimer's "Swedish" mutant APP overexpressing mice (Tg2576 line) with luteolin results in a significant reduction in Aβ generation. Data show that luteolin treatment achieves this reduction through selective inactivation of the GSK-3α isoform. As in vivo validation, administration of luteolin to Tg2576 mice similarly reduces Aβ generation through GSK-3 inhibition.

In another embodiment, GSK-3β phosphorylates APP and PS1, contributing to Aβ mediated neurotoxicity. Moreover, γ-secretase cleaves downstream proteins of APP processing, resulting in generation of either major form of the Aβ peptide ($A\beta_{1-40, 42}$). Flavonoids efficiently inhibit proper association of the γ-secretase complex, through increased phosphorylation of presenilin 1 (PS1), preventing APP processing. Flavones, including lutoelin, disomin, and diosmetin were found to efficiently abrogate γ-secretase complex, preventing PS1 from associating with other γ-secretase complex components.

Many amyloid diseases are characterized by amyloid protein entanglement. In normally functioning brains, Tau associates with tubulin thereby stabilizing microtubules. However, when tau becomes hyperphosphorylated, the hyperphosphorylated peptides aggregate into paired helical filaments, which amass in nerve cell bodies as neurofibrillary tangles and dystrophic neuritis of amyloid plaques. In another embodiment, flavonoids, especially flavones, inhibit the activity of GSK-3, thereby preventing tau hyperphosphotrylation. Preferably, the flavonoids are either lutoelin, disomin, or diosmetin.

The treatment methods discussed above are effective at treating amyloid diseases. The treatments are effective and treating and preventing Alzheimer's Disease, Huntington's Disease, and type II diabetes.

BRIEF DESCRIPTION OF THE DRAWINGS

For a fuller understanding of the invention, reference should be made to the following detailed description, taken in connection with the accompanying drawings, in which.

Figure 26:
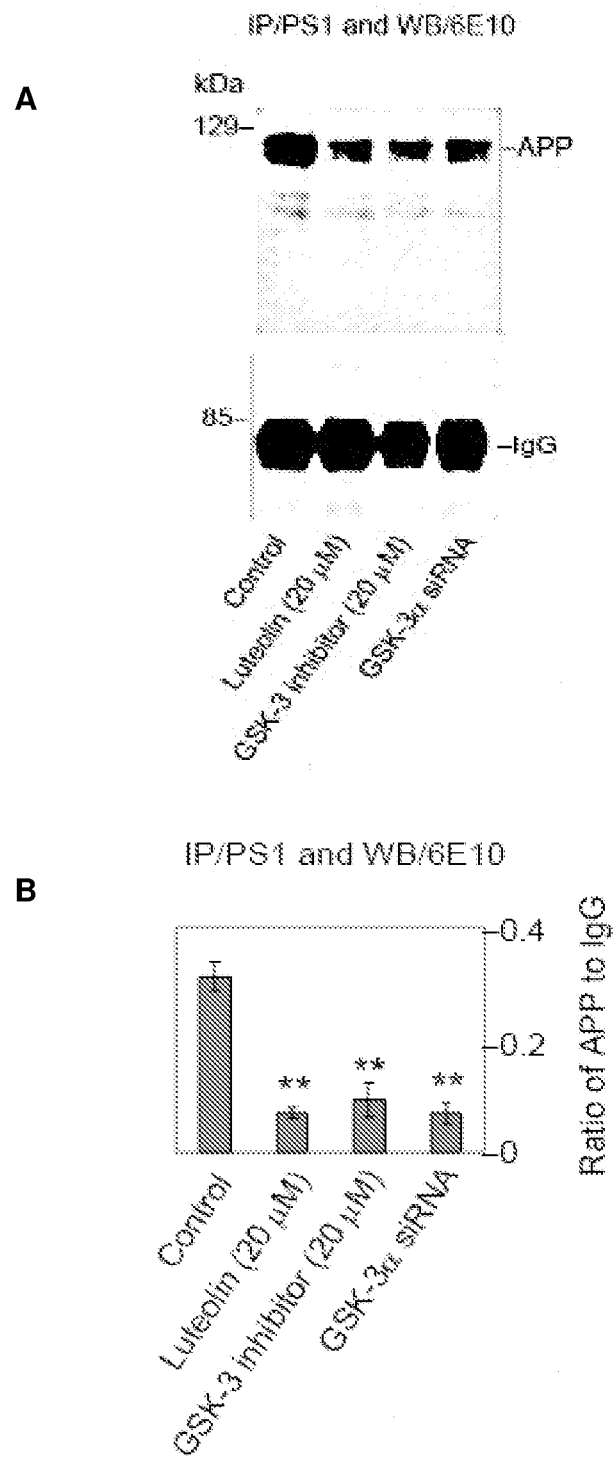

FIG. 26 depicts GSK-3α regulates PS1-APP association. SweAPP N2a cells were treated with either luteolin (20 μm) GSK-3 inhibitor SB-415286 (20 μm) for 4 hrs or transfected with GSK-3α siRNA. (A) Lysates were immunoprecipitated by anti-PS1 CTF antibody and analyzed using Western blot. 6E10 antibodies were used to probe the Western blot. (B) Densitometric analysis of Western blot shows the ratio of APP to IgG as indicated. At test revealed significant differences between all treatments and control (P<0.001 with n=3 for each condition).

Figure 27:
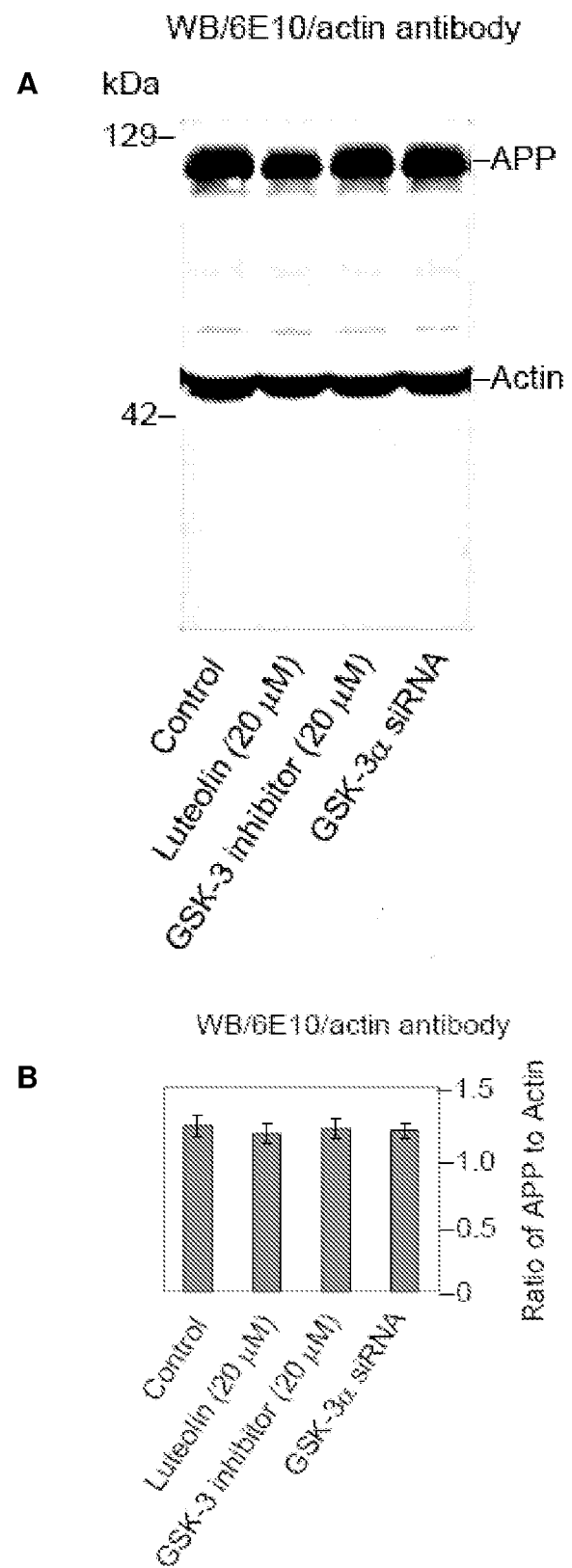

FIG. 27 depicts GSK-3α regulation of PS1-APP association. SweAPP N2a cells were treated with either luteolin (20 μm), GSK-3 inhibitor SB-415286 (20 μm) for 4 hrs, or transfected with GSK-3α siRNA. Cell lysates from these treated cells and GSK-3α siRNA-transfected cells were subsequently analyzed by immunoprecipitation/Western blot. (A) Cell lysates were analyzed by Western blot by 6E10 antibody. (B) Densitometric analysis of Western blot against anti-actin antibody-stained control reveals no significant changes in the ratio of APP to actin as indicated (P>0.05).

Figure 28:
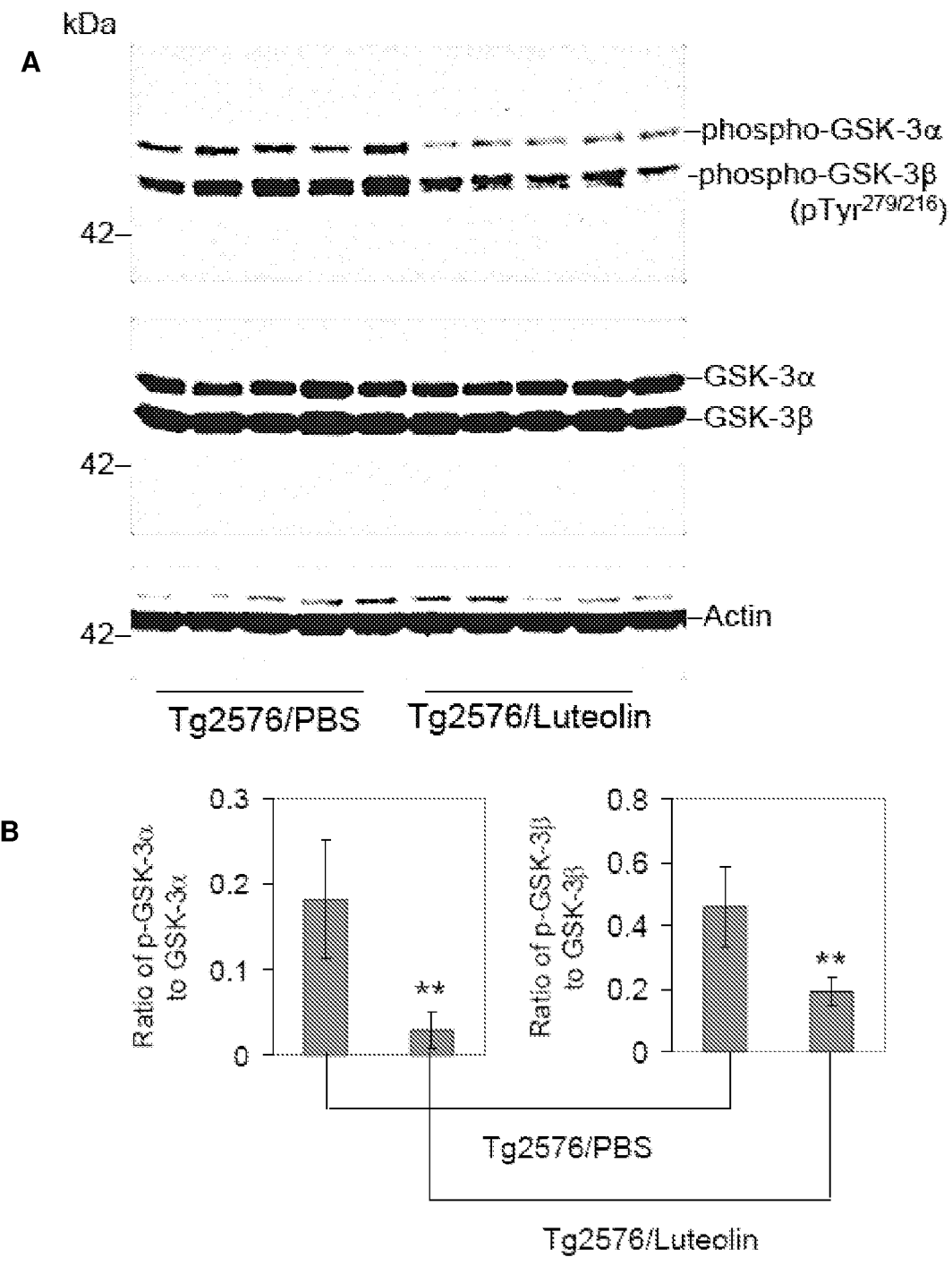

FIG. 28 depicts GSK luteolin inhibiting GSK-3 activation and cerebral amyloidosis in Tg2576 mice. Brain homogenates from Tg2576 mice treated with luteolin (n=5) or vehicle (PBS, n=5) and analyzed. (A) Western blot of brain homogenates with active and holo anti-GSK-3 antibodies with anti-actin antibodies as an internal control. (B) A densitometric graph revealing the ratio of active phosphorylated GSK-3α/β to holo GSK-3. At test reveals significant reductions in both active GSK-3α and β isoforms from luteolin treated animals compared to control (P<0.001).

Figure 29:
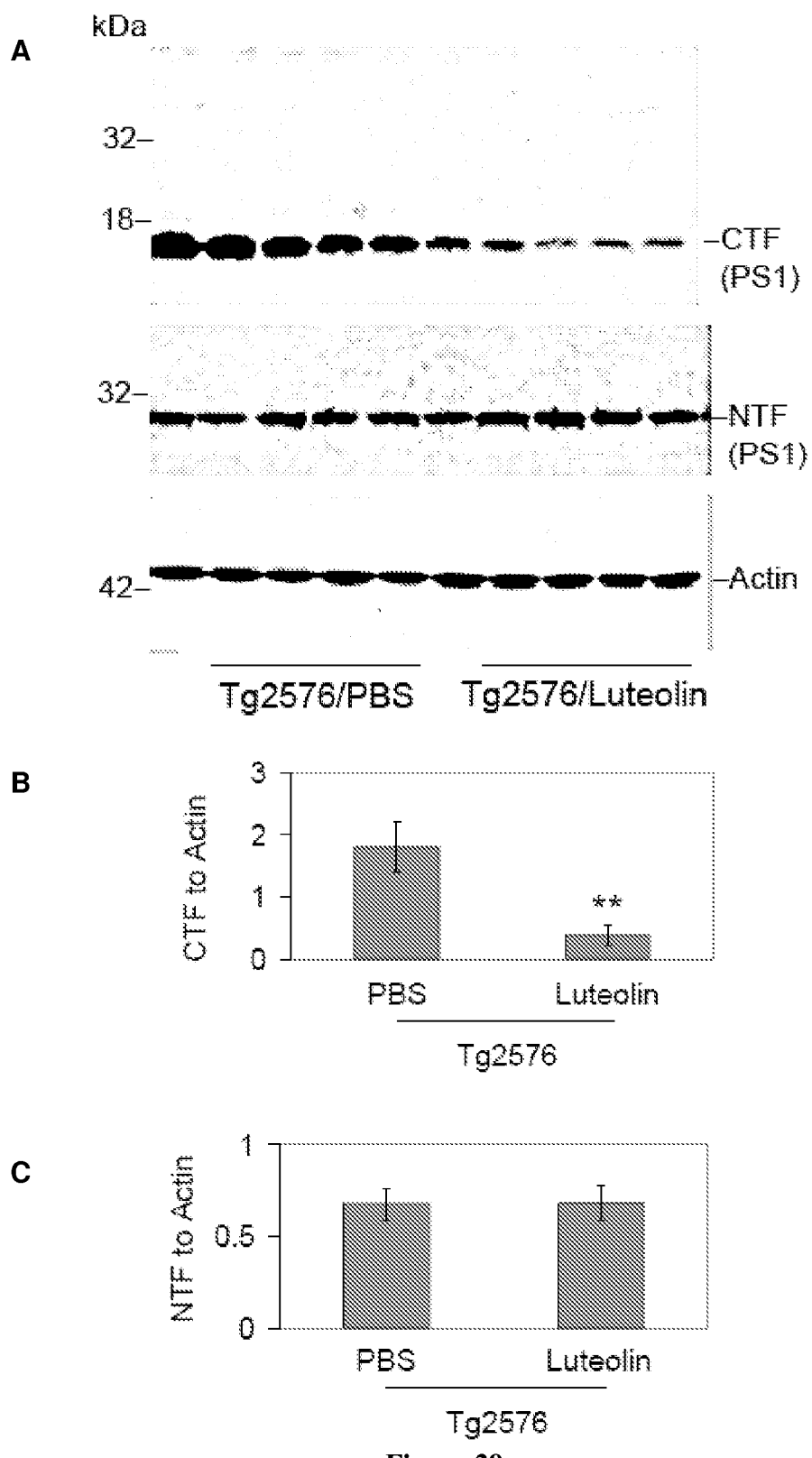

FIG. 29 show luteolin inhibits GSK-3 activation and cerebral amyloidosis in Tg2576 mice. Brain homogenates from Tg2576 mice treated with luteolin (n=5) or vehicle (PBS, n=5) and analyzed. (A) Western blot of brain homogenates were performed using anti-PS1 CTF or NTF antibody. Densitometric analysis produces the ratio of (B) PS1 CTF or (C) PS1 NTF to actin (internal control). At test shows significant reductions in PS1 CTF levels with luteolin treatment (P<0.001), but not for PS1 NTF levels (P>0.05).

Figure 30:
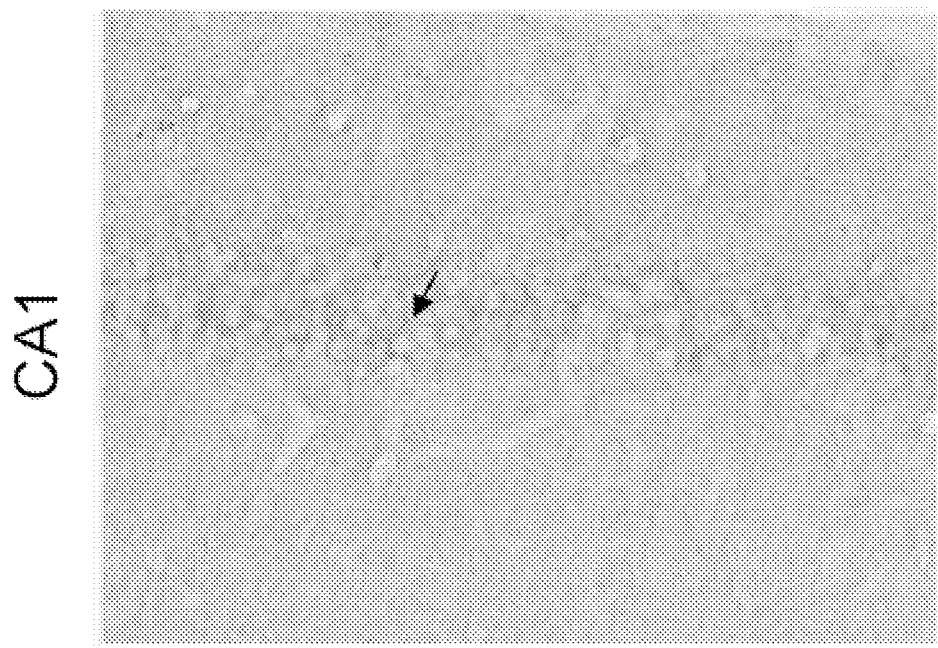

FIG. 30 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.

Figure 31:
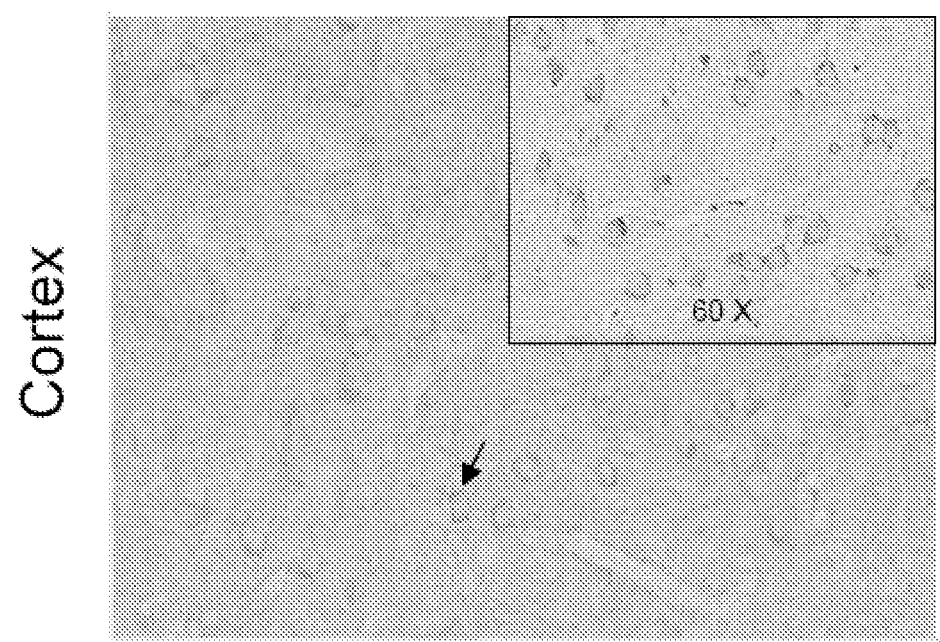

FIG. 31 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.

Figure 32:

FIG. 32 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.

Figure 33:
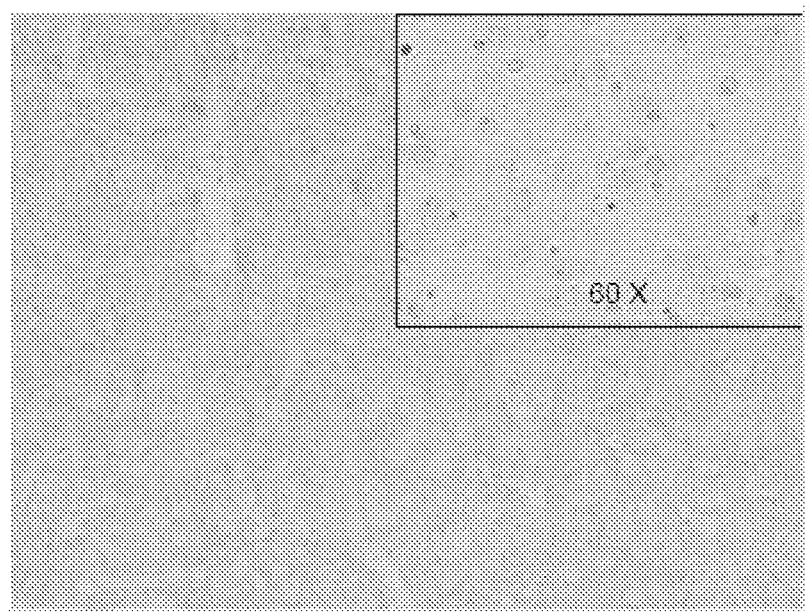

FIG. 33 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.

Figure 34:
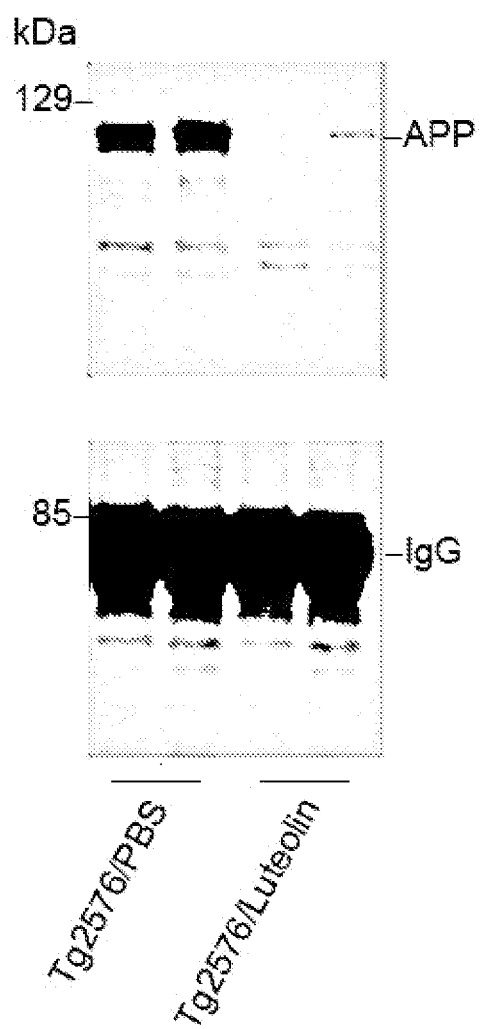

FIG. 34 is a blot depicting luteolin administration abrogates APP-PS1 interaction and indicating luteolin inhibits GSK-3 activation and cerebral amyloidosis in Tg2576 mice. Homogenates were immunoprecipitated by anti-PS1 CTF antibody and subjected to 6E10-probed Western blot. After administration of luteolin, APP signals disappear or drop sharply, indicating APP cannot adequately bind to PS1.

Figure 35:
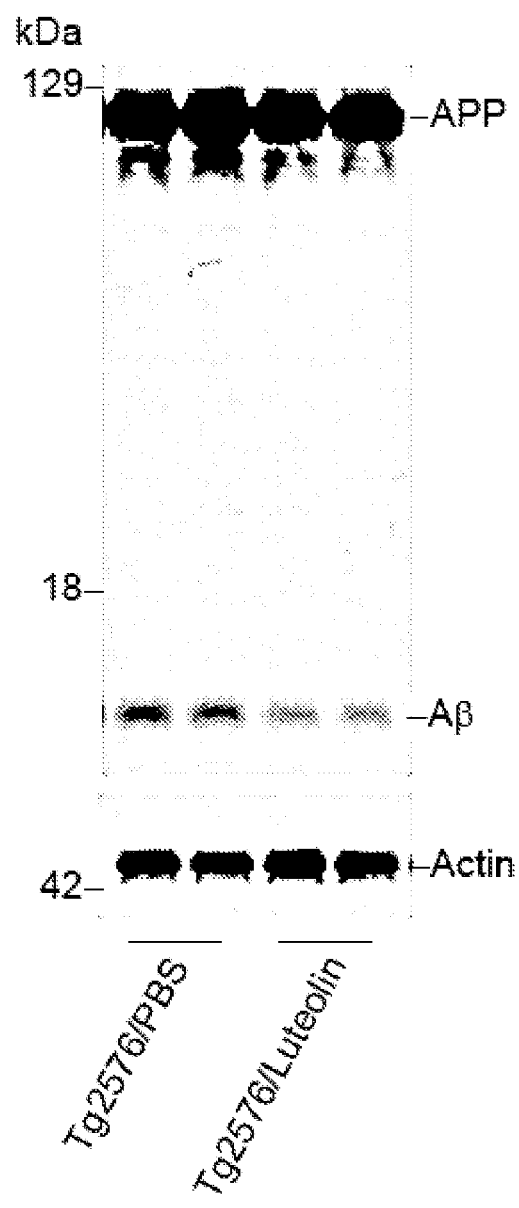

FIG. 35 is a blot showing luteolin administration does not impact APP precipitation. Homogenates were immunoprecipitated using 6E10 antibody and subjected to 6E10-probed Western blot. Administration of luteolin does not impact APP signals. Approximately 12 kD band may represent oligomeric form of amyloid.

Figure 36:
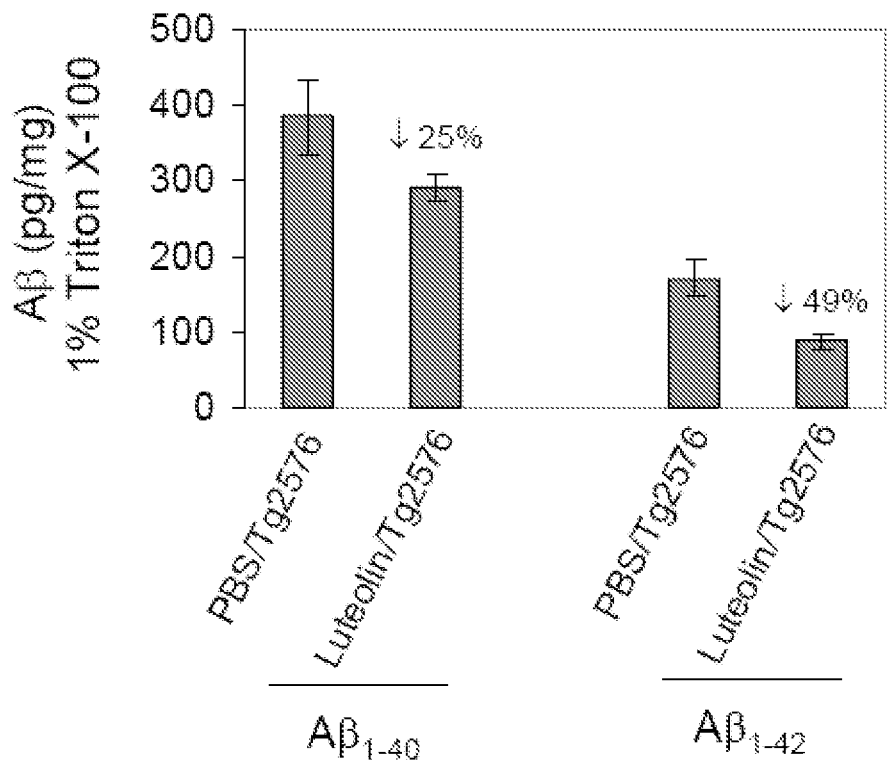

FIG. 36 is a graph of soluble and insoluble $A\beta_{1-40, 42}$ peptides from homogenates analyzed by ELISA. For Aβ ELISA, data are represented as picograms of peptide present in milligrams of total protein. Luteolin treatment results in markedly reduced soluble $A\beta_{1-40, 42}$ levels, 25% and 49%, respectively.

Figure 37:
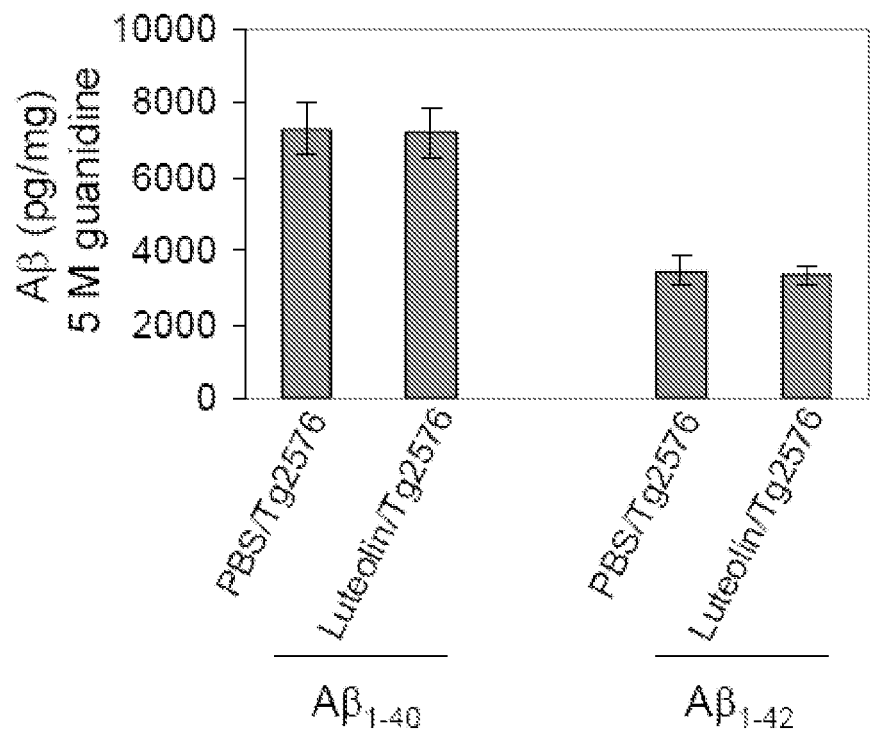

FIG. 37 is a graph of soluble and insoluble $A\beta_{1-40, 42}$ peptides from homogenates analyzed by ELISA. For Aβ ELISA, data are represented as picograms of peptide present in milligrams of total protein. No significant reductions in insoluble Aβ isoforms following treatment were observed.

DETAILED DESCRIPTION OF THE PREFERRED EMBODIMENT

Amyloid diseases, such as Alzheimer's Disease, Huntington's Disease, and type II diabetes, are debilitating diseases resulting from cellularly processed protein agglomerates. Flavonoids were found to selectively inhibit GSK-3 activity, preventing PP1 and PS-1 phosphorylation and inactivating gamma secretase. The flavonoids attenuate Aβ generation and possesses the ability to protect against the multiple arms of AD pathology. Flavonoids also efficiently inhibit proper association of the γ-secretase complex, through increased phosphorylation of presenilin 1 (PS1), preventing APP processing and inhibit the activity of GSK-3, thereby preventing tau hyperphosphotrylation.

Sixteen (8♂/8♀) Tg2576 mice (Taconic, Germantown, N.Y.) were used; 8 mice received luteolin, and the other 8 received phosphate buffered saline (PBS). Beginning at 8 months of age, Tg2576 mice were intraperitoneally injected with luteolin (20 mg/kg) or PBS daily for 30 days based on previously described methods (39). These mice were then sacrificed at 9 months of age for analyses of Aβ levels and Aβ load in the brain according to previously described methods (59). Animals were housed and maintained in the College of Medicine Animal Facility at the University of South Florida (USF), and all experiments were in compliance with protocols approved by the USF Institutional Animal Care and Use Committee.

Western Blot and Immunoprecipitation

Figure 1:
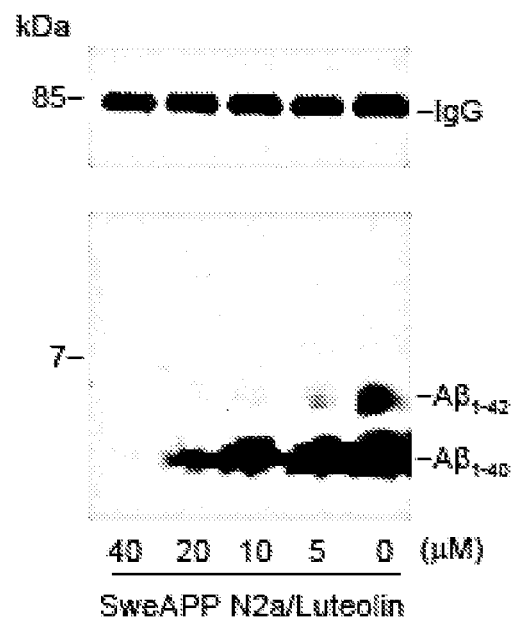
FIG. 1 is a western blot depicting luteolin reducing Aβ generation and decreasing γ-secretase cleavage activity in cultured neuronal cells. SweAPP N2a cells were treated with luteolin at various doses as indicated for 12 hrs. Secreted Aβ$_{1-40, 42}$ peptides were analyzed by immunoprecipitation and Western blot.
Figure 2:
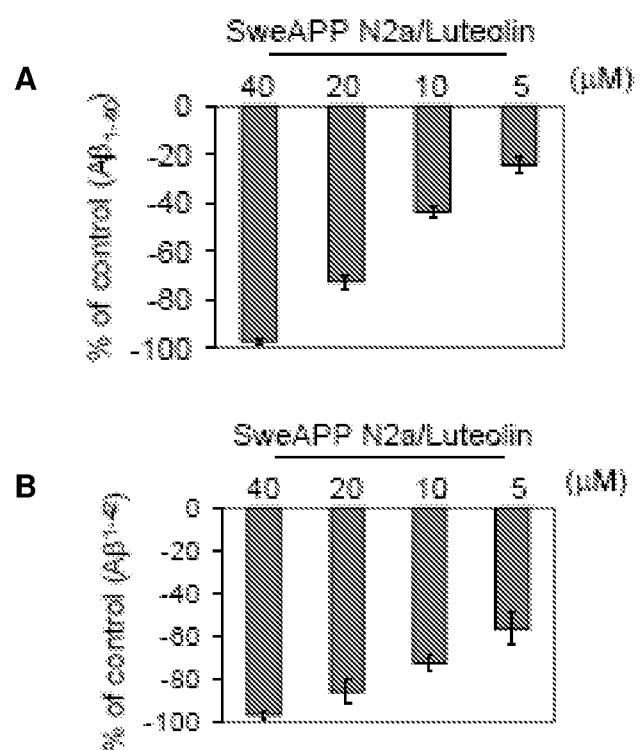
FIG. 2 shows luteolin reduces Aβ generation and decreases γ-secretase cleavage activity in cultured neuronal cells. SweAPP N2a cells were treated with luteolin at various doses as indicated for 12 hrs. Secreted (A) Aβ$_{1-40}$ peptides or (B) Aβ$_{1-42}$ were analyzed by ELISA (left; n=3 for each condition) in conditional media. For Aβ ELISA, data are represented as a percentage of Aβ$_{1-40}$ peptides secreted 12 hrs after luteolin treatment relative to control (untreated).
Figure 3:
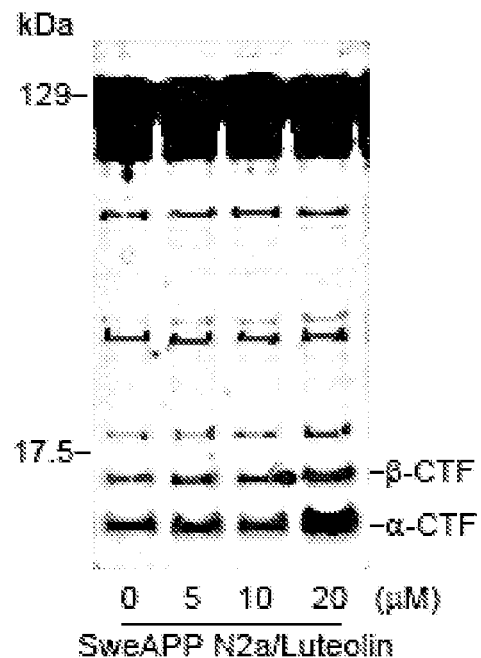
FIG. 3 is a blot showing luteolin reducing Aβ generation and decreasing γ-secretase cleavage activity in cultured neuronal cells. SweAPP N2a cells were treated with luteolin at various doses as indicated for 12 hrs. APP CTFs were analyzed by Western blot in cell lysates and relative fold mean over. One-way ANOVA followed by post hoc comparison revealed significant differences between each dose (P<0.005) except between 20 μM and 40 μM (P>0.05).
Figure 4:
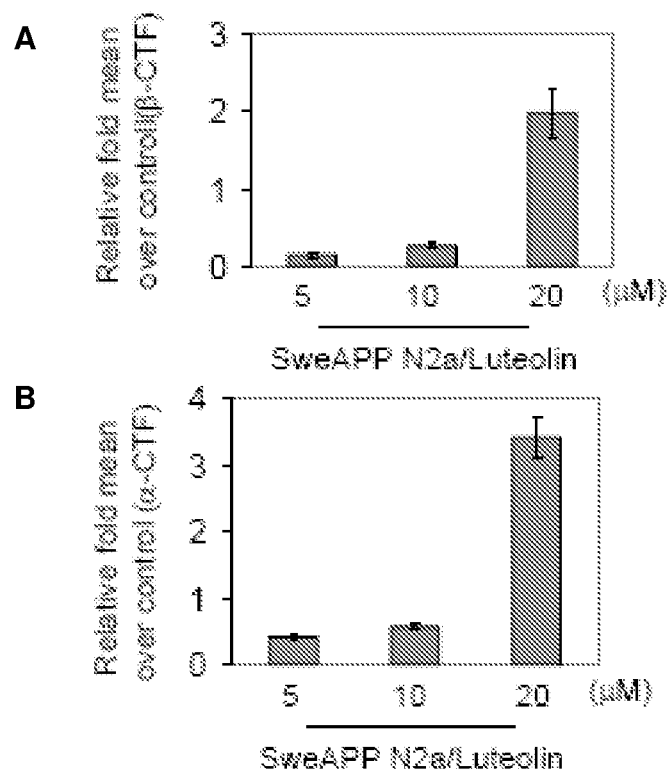
FIG. 4 is a bar graph of the blot in FIG. 3, and depicting luteolin reducing Aβ generation and decreasing γ-secretase cleavage activity in cultured neuronal cells. SweAPP N2a cells were treated with luteolin at various doses as indicated for 12 hrs. The relative fold mean over control for (A) β-CTF and (B) α-CTF was calculated by Densitometry analysis and graphed. One-way ANOVA followed by post hoc comparison revealed significant differences between each dose (P<0.005) except between 20 μM and 40 μM (P>0.05). SweAPP N2a cells were treated with luteolin at a single dose (20 μM) for various time points as indicted.
Figure 5:
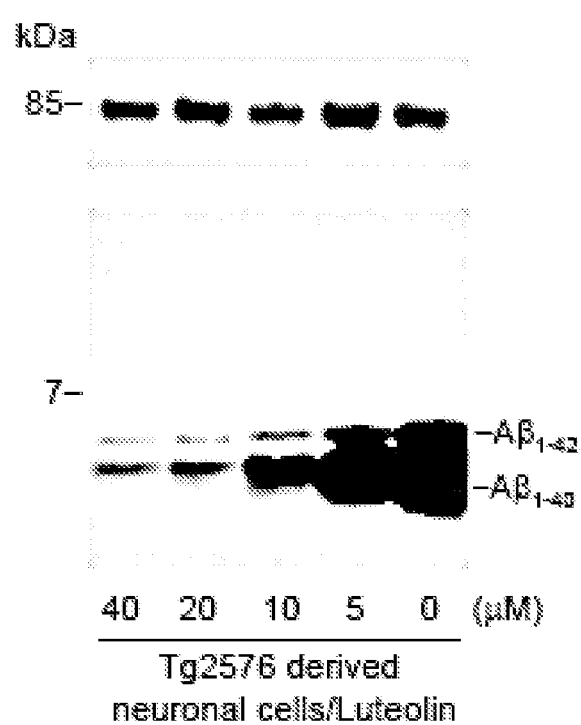
FIG. 5 is a blot depicting luteolin reducing Aβ generation and decreasing γ-secretase cleavage activity in cultured neuronal cells. Tg2576 derived neuronal cells were treated with luteolin at various doses as indicated for 12 hrs. Secreted Aβ$_{1-42}$ peptides were analyzed by immunoprecipitation and Western in conditional media. For Aβ ELISA, data are represented as a percentage of Aβ$_{1-40, 42}$ peptides secreted 12 hrs after luteolin treatment relative to control (untreated).
Figure 6:
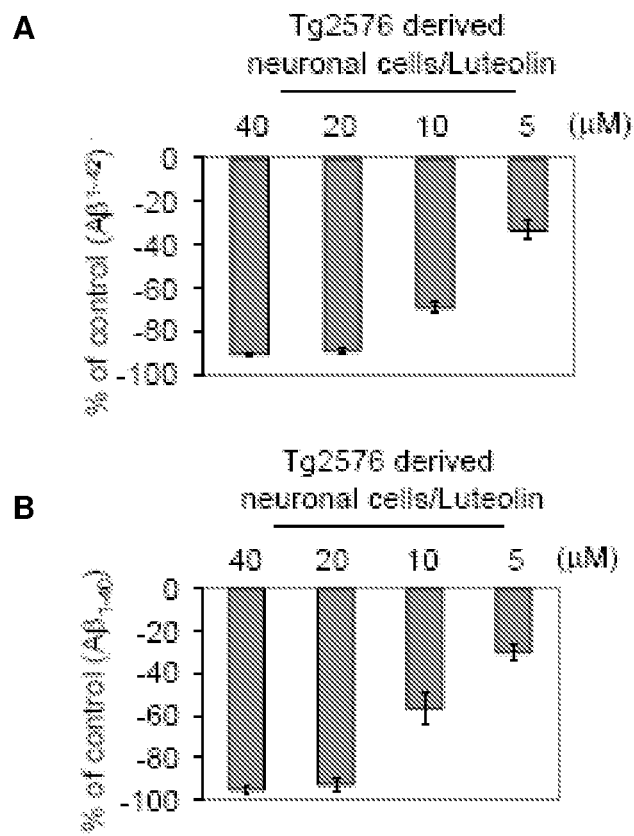
FIG. 6 is a graph of the blot in FIG. 5, and showing luteolin reducing Aβ generation and decreasing γ-secretase cleavage activity in cultured neuronal cells. Tg2576 derived neuronal cells were treated with luteolin at various doses as indicated for 12 hrs. Secreted (A) Aβ$_{1-42}$ or (B) Aβ$_{1-40}$ peptides were analyzed by ELISA (left; n=3 for each condition) in conditional media. For Aβ ELISA, data are represented as a percentage of Aβ$_{1-40, 42}$ peptides secreted 12 hrs after luteolin treatment relative to control (untreated).
Figure 7:
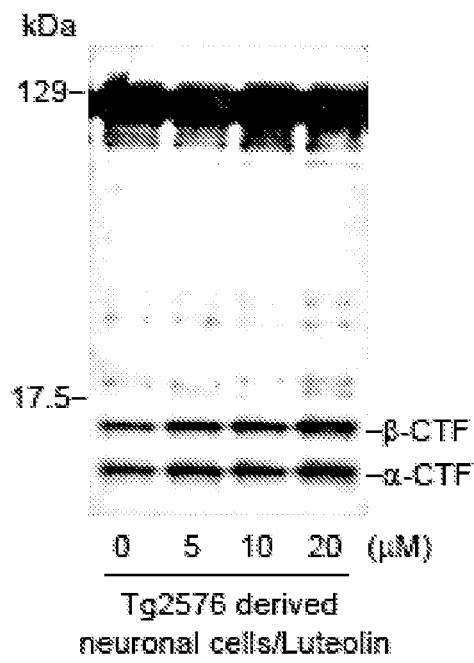
FIG. 7 is a blot showing luteolin reducing Aβ generation and decreasing γ-secretase cleavage activity in cultured neuronal cells. Tg2576 derived neuronal cells were treated with luteolin at various doses as indicated for 12 hrs. APP CTFs were analyzed by Western blot in cell lysates
Figure 8:
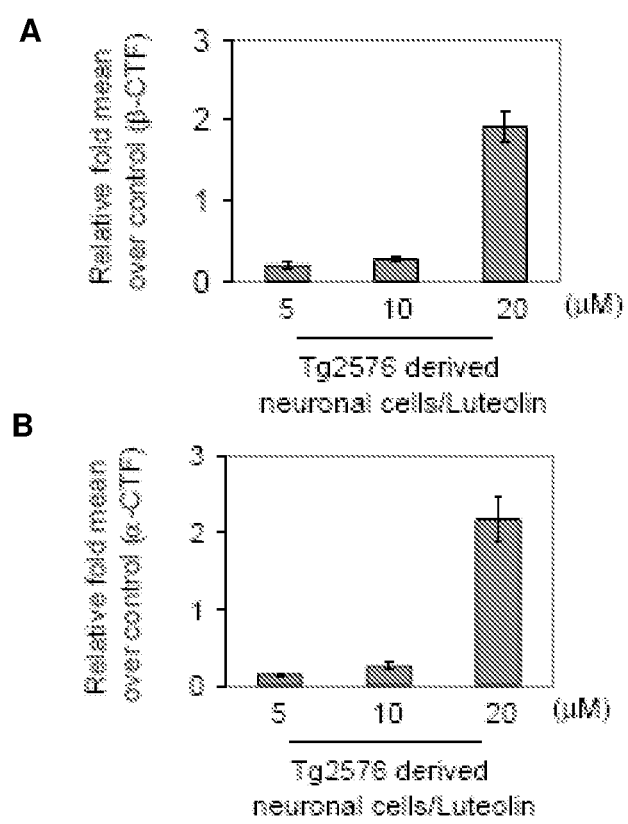
FIG. 8 is a graph of the signal strength of the blot in FIG. 7, and depicting luteolin reducing Aβ generation and decreasing γ-secretase cleavage activity in cultured neuronal cells. Tg2576 derived neuronal cells were treated with luteolin at various doses as indicated for 12 hrs. APP CTFs were analyzed by Western blot and relative fold mean over control (A) β-CTF or (B) α-CTF was calculated by Densitometry analysis. One-way ANOVA followed by post hoc comparison revealed significant differences between each dose (P<0.005) except between 20 μM and 40 μM (P>0.05). SweAPP N2a cells were treated with luteolin at a single dose (20 μM) for various time points as indicted.
Figure 9:
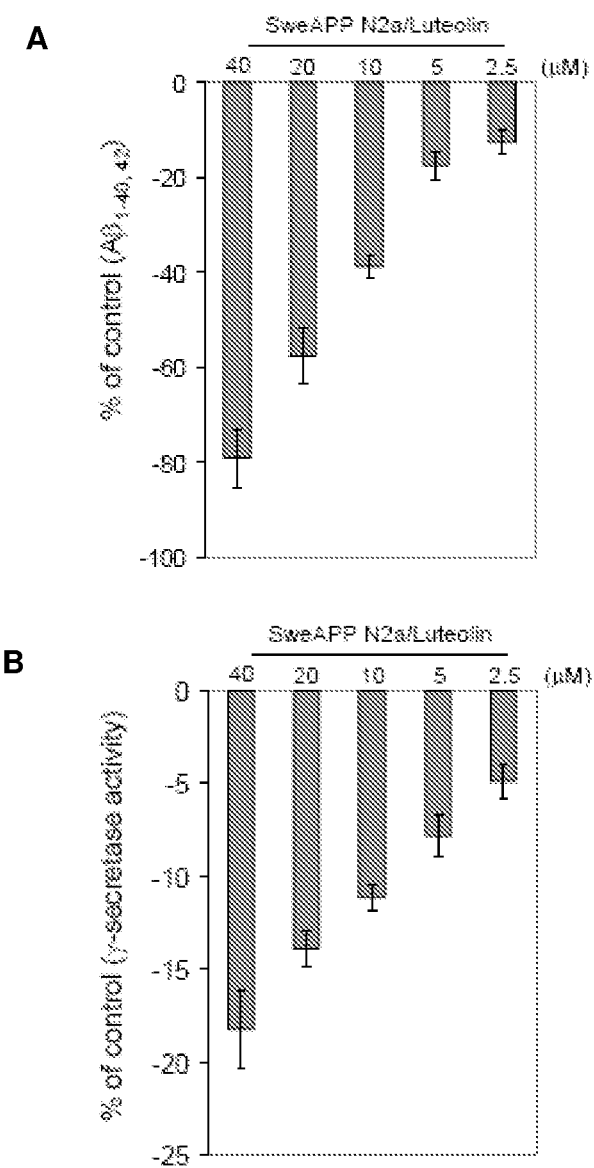
FIG. 9 is a graph of luteolin reducing Aβ generation and decreasing γ-secretase cleavage activity in cultured neuronal cells in a dose dependent manner. (A) Secreted Aβ$_{1-40, 42}$ peptides were analyzed in conditional media by ELISA, (n=3 for each condition). (B) γ-secretase activity was analyzed in cell lysates using secretase cleavage activity assay, (n=3 for each condition). Data was presented as a percentage of fluorescence units/milligrams protein activated 30, 60, 90, 120, 300 min after luteolin treatment relative to control (untreated). A difference was noted between each time point examined (P<0.005). In parallel, a structurally similar compound, apigenin was used as control. However, results were not similar to luteolin (data not shown).
Figure 10:
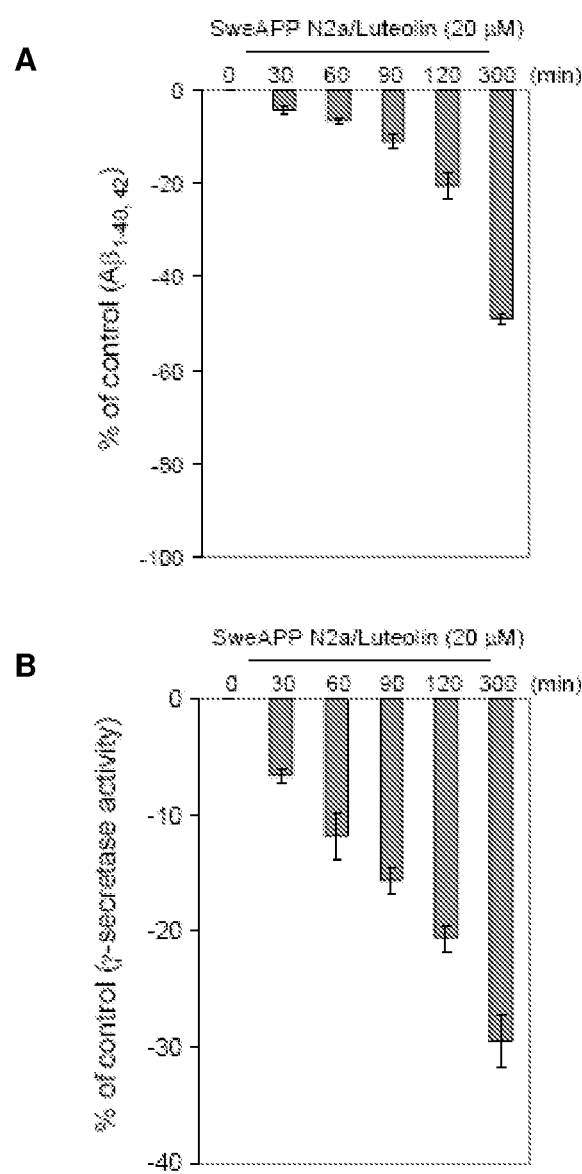
FIG. 10 is a graph showing luteolin reduces Aβ generation and decreases γ-secretase cleavage activity in cultured neuronal cells in a time-dependent manner SweAPP N2a cells were treated with luteolin at a single dose (20 μM) for various time points as indicted. (A) Secreted Aβ$_{1-40, 42}$ peptides were analyzed in conditional media by ELISA, (n=3 for each condition). (B) γ-secretase activity was analyzed in cell lysates using secretase cleavage activity assay, (n=3 for each condition). Data presented as a percentage of fluorescence units/ milligrams protein activated 30, 60, 90, 120, 300 min after luteolin treatment relative to control (untreated). A difference was noted between each time point examined (P<0.005). In parallel, a structurally similar compound, apigenin was used as control. However, results were not similar to luteolin (data not shown).
Figure 11:
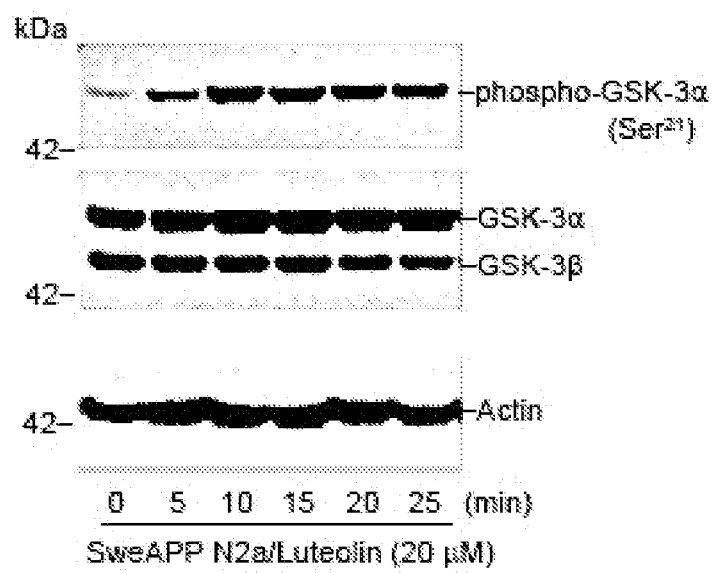
FIG. 11 is a blot showing luteolin selectively inactivates GSK-3α. SweAPP N2a cells were treated with luteolin at 20 μM for various time points as indicated. Cell lysates were prepared and subjected to Western blot analysis in phosphorylated forms of GSK-3α/β. Western blot analysis using anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Western blot analysis using anti-actin antibody shows actin protein (as an internal reference control). Densitometry analysis shows the ratio of phospho-GSK-3α (Ser$^{21}$) to total GSK-3α as indicated below the figures (n=3 for each condition).
Figure 12:
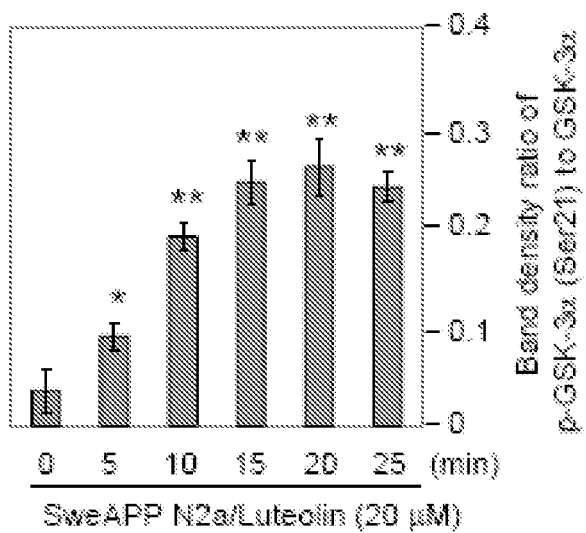
FIG. 12 is a graph of the blot in FIG. 11, and showing signal ratios of p-GSK-3α. SweAPP N2a cells were treated with luteolin at 20 μM for various time points as indicated. Cell lysates were prepared and subjected to Western blot analysis in phosphorylated forms of GSK-3α/β and one-way ANOVA followed by post hoc comparison revealed a significant difference between 0 min and 5, 10, 15, 20 or 25 min (P<0.001). Anti-actin antibody was used as internal reference control.

Cultured cells or mouse brain were lysed in ice-cold lysis buffer described above, and an aliquot corresponding to 50 μg of total protein was electrophoretically separated using 12% Tris-HCl or 16.5% Tris-tricine gels. Electrophoresed proteins were then transferred to PVDF membranes, washed in dH$_2$O, and blocked for 1 hr at ambient temperature in Tris-buffered saline (TBS; Bio-Rad) containing 5% (w/v) non-fat dry milk. After blocking, membranes were hybridized for 1 hr at ambient temperature with various primary antibodies. Membranes were then washed 3× for 5 min each in dH$_2$O and incubated for 1 hr at ambient temperature with the appropriate HRP-conjugated secondary antibody (1:1,000). Antibodies were obtained against the amino-terminus and carboxyl-terminus of PS1 (Chemicon, Temecula, Calif.), amino-terminus and carboxyl-terminus of APP (22C11), actin (Roche, Basel, Switzerland), Aβ (6E10, 48G) (Signet Laboratories, Dedham, Mass.), phosphor-GSK3α (ser$^{21}$, clone BK202) (Upstate, Lake Placid, N.Y.), phospho-GSK3α/β (pTyr$^{279/216}$) (Sigma), phospho-GSK-3β (Ser$^9$) (Sigma) and total GSK-3α/β (Sigma). All antibodies were diluted in TBS containing 5% (w/v) of non-fat dry milk Blots were developed using the luminol reagent (Pierce Biotechnology). Densitometric analysis was done as previously described using a FluorS Multiimager with Quantity One™ software (39) Immunoprecipitation was performed for detection of sAPP-α, sAPP-β and Aβ by incubating 200 μg of total protein of each sample with various sequential combinations of 6E10 (1:100) and/or 22C11 (1:100) antibodies overnight with gentle rocking at 4° C., and 10 μL of 50% protein A-Sepharose beads were then added to the sample (1:10; Sigma) prior to gentle rocking for an additional 4 hrs at 4° C. Following washes with 1× cell lysis buffer, samples were subjected to Western blot as described above. Antibodies used for Western blot included the APP-carboxyl-terminal antibody (1:50)), amino-terminal APP antibody (clone 22C11), or 6E10 (1:1,000), or actin antibody (1:1,500; as an internal reference control). γ-secretase activity was quantified in cell lysates using available kits based on secretase-specific peptides conjugated to fluorogenic reporter molecules.
ELISA Cultured cells were lysed in ice-cold-lysis buffer (20 mM Tris, pH 7.5, 150 mM NaCl, 1 mM EDTA, 1 mM EGTA, 1% v/v Triton X-100, 2.5 mM sodium pyropgosphate, 1 mM β-glycerolphosphate, 1 mM $Na_3VO_4$, 1 μg/mL leupeptin, 1 mM PMSF). Mouse brains were isolated under sterile conditions on ice and placed in ice-cold lysis buffer. Brains were then sonicated on ice for approximately 3 min, allowed to stand for 15 min at 4° C., and centrifuged at 15,000 rpm for 15 min $Aβ_{1-40, 42}$ ELISA kits were obtained from IBL-American (Minneapolis, Minn.). $Aβ_{1-40, 42}$ species were detected by acid extraction of brain homogenates in 5 M guanidine buffer (39), followed by a 1:10 dilution in lysis buffer. Soluble $Aβ_{1-40, 42}$ were directly detected in cultured cell lysates or brain homogenates prepared with lysis buffer described above by a 1:4 or 1:10 dilution, respectively. $Aβ_{1-40, 42}$ was quantified in these samples using the $Aβ_{1-40, 42}$ ELISA kits in accordance with the manufacturer's instructions, except that standards included 0.5 M guanidine buffer in some cases.
Luteolin Inhibits $Aβ_{1-40, 42}$ Generation from SweAPP N2a Cells and Tg2576 Mouse-Derived Primary Neuronal Cells SweAPP N2a cells and primary neuronal cells derived from Tg2576 mice were treated with varying doses of luteolin to examine luteolin's effect on APP proteolysis. Cellular extracts were collected and analyzed using immunoprecipitation (IP), Western blot, and ELISA. Luteolin (>95% purity by HPLC), (Sigma, St Louis, Mo.), effectively reduced $Aβ_{1-40, 42}$ production in either cell line in a dose dependent manner, shown in FIGS. 1 through 2(B) and 5 through 6(B), and abrogated $Aβ_{1-40, 42}$ peptide generation >70% and >85% at doses of 20 and 40 μM, respectively. See FIGS. 1 through 2(B) and 5 through 6(B). SweAPP N2a and primary Tg2576-derived neuronal cells CTF profiles were analyzed following luteolin treatment to determine at which level luteolin impacts amyloid processing. As illustrated in FIGS. 3 though 4(B) and 7 though 8(B), Western blot analysis shows a dose dependent accumulation of both α and β CTFs, approximately 2-3 fold increases in either cell line.

Due to the implications on γ-secretase activity, luteolin's effect on SweAPP N2a cells was analyzed using a fluorometric assay for γ-cleavage. Luteolin lowered γ-secretase cleavage activity in both a dose and time dependent fashion, depicted in FIGS. 9(A) through 10(B). These dose and time dependent decreases in γ-secretase cleavage activity correlate with decreases in total Aβ generation, seen in FIGS. 9(A) through 10(B), which suggests that luteolin exerts its anti-amyloidogenic effects through down-regulation of γ-secretase activity.
Luteolin Selectively Inactivates GSK-3α/β in SweAPP N2a Cells and Tg2576 Mouse-Derived Primary Neuronal Cells The effect luteoline had on a variety of proteins related to and/or required for proper functioning of the γ-secretase complex was evaluated to establish the mechanism whereby luteolin modulates γ-secretase activity and subsequent Aβ generation. Luteolin (20 μM) increased the levels of serine 21-phosphorylated, inactive GSK-3α isoforms in both SweAPP N2a and primary Tg2576-derived neuronal cells, depicted in FIGS. 12 through 18. However, no significant changes were observed in overall expression of either GSK3-α or β by Western blot, confirming that this phenomenon most likely occurs at the post-translational or protein stage of this kinase. See, FIGS. 12 through 18. This increase in GSK-3α serine 21 residue phosphorylation-mediated inactivation continued through 3 hrs, shown in FIGS. 13 and 17, while the levels of tyrosine 279 phosphorylated active GSK-3α isoforms concurrently decreased in time-dependent manner, shown in FIGS. 13 and 17). More to the point, these time-dependent decreases in phospho-tyrosine 279 active GSK-3α are quite congruent with the increases seen with phospho-serine 21 inactive isoforms. See, FIGS. 12 through 18. FIGS. 14 and 18 indicate abrupt decreases in active phosphorylated isoforms, with concurrent increases in inactive phosphorylated isoforms within 60 minutes of luteolin treatment. Following 2 hours of luteolin treatment, phospho-tyrosine 216 GSK-3α active levels decline. Therefore, luteolin affects GSK-3α/β signaling and confirms that this signaling is a potential upstream event required for modulation of γ-secretase activity.

Example 1

GSK-3 Inhibition Alters PS1
Processing/Phosphorylation in SweAPP N2a Cells

Cultured cells or mouse brain were lysed in ice-cold lysis buffer described above, and an aliquot corresponding to 50 μg of total protein was electrophoretically separated using 12% Tris-HCl or 16.5% Tris-tricine gels. Electrophoresed proteins were then transferred to PVDF membranes, washed in $dH_2O$, and blocked for 1 hr at ambient temperature in Tris-buffered saline (TBS; Bio-Rad) containing 5% (w/v) non-fat dry milk. After blocking, membranes were hybridized for 1 hr at ambient temperature with various primary antibodies. Membranes were then washed 3× for 5 min each in $dH_2O$ and incubated for 1 hr at ambient temperature with the appropriate HRP-conjugated secondary antibody (1:1,000). All antibodies were diluted in TBS containing 5% (w/v) of non-fat dry milk. Blots were developed using the luminol reagent (Pierce Biotechnology). Densitometric analysis was done as previously described using a FluorS Multiimager with Quantity One™ software. Immunoprecipitation was performed for detection of sAPP-α, sAPP-β and Aβ by incubating 200 μg of total protein of each sample with various sequential combinations of 6E10 (1:100) and/or 22C11 (1:100) antibodies overnight with gentle rocking at 4° C., and 10 μL of 50% protein A-Sepharose beads were then added to the sample (1:10; Sigma) prior to gentle rocking for an additional 4 hrs at 4° C. Following washes with 1× cell lysis buffer, samples were subjected to Western blot as described above. Antibodies used for Western blot included the APP-carboxyl-terminal antibody (1:50)), amino-terminal APP antibody (clone 22C11), or 6E10 (1:1,000), or actin antibody (1:1,500; as an internal reference control). γ-secretase activity was quantified in cell lysates using available kits (R&D Systems, Minneapolis, Minn.). based on secretase-specific peptides conjugated to fluorogenic reporter molecules.

FIGS. 19(A) through 23 depict the Western blot analysis of carboxyl-terminal portions of PS1 reveals three distinct bands. The two bands of highest molecular weight, approximately 20 kD and 18 kD in size, represent phosphorylated PS1 CTFs with a smaller 16 kD band representing the more common CTF product indicative of PS1 endoproteolytic cleavage. Following SweAPP N2a cell treatment with luteolin, PS1 CTF phosphorylation increases. Phospho-PS1 CTF to PS1 CTF ratios differ significantly with luteolin treatment, both dose and time-dependently, depicted in FIG. 19(A) through (C), and correlate with the dose and time-dependent decreases in $A\beta_{1-40, 42}$ generation.

To confirm that the 20 kD and 18 kD bands were phosphorylated PS1 isoforms, SweAPP N2a cells were treated with luteolin (20 μM) prior to lysis and cell lysates incubated with calf intestine alkaline phosphatase (CIAP) (Fermentas, Hanover, Md.), to dephosphorylate any potential phosphorylated proteins, to eliminate skewing of electrophoretic mobilities. Following 30 minutes of incubation, the 20 kD band is not evident in the CIAP treated lysates, seen in FIGS. 21(A) through 22, and the 18 kD band reduced while endogenous CTF, 16 kD, appears to accumulate. When compared to lysates incubated with only reaction buffer, phosphorylated residues decrease in a time dependent manner, showing by the 20 kD CTF:16 kD CTF. See FIGS. 21(A) and (B). While luteolin treatment influenced PS1 CTF species, luteolin had no significant effect on either full-length PS1 or PS1 NTF protein levels. See FIGS. 23(A) and (B). Luteolin affects PS1 phosphorylation and may indicate a means by which γ-secretase activity may be regulated.

To determine if this phenomenon was specifically attributable to luteolin treatment or more generally in regards to GSK-3 inhibition, SweAPP N2a cells were treated with a range of doses of the GSK-3 inhibitor SB-415286 (BIOMOL®, Plymouth Meeting, Pa.). See FIG. 24(A). Alterations in phospho-PS1 CTF:PS1 CTF ratios were similar to prior experiments and congruent decreases in $A\beta_{1-40, 42}$ generation with SB-415286 treatment were confirmed. FIG. 24(B). GSK-3α and β was successfully knocked-down (>70%, data not shown) with siRNA in SweAPP N2a cells, substantiating the role of GSK-3α in this luteolin-mediated PS1 processing. GSK-3α siRNA transfected cells exhibit significantly higher phosphorylated PS1 isoforms as compared to GSK-3β siRNA or mock transfectants, shown in FIG. 25(A); P<0.001). Similar differences were observed when comparing the level of PS1 phosphorylation in luteolin treated (20 μM) cells to that of GSK-3β siRNA or mock transfectants. See FIG. 25(B); P<0.001), illustrating GSK-3α regulates PS1 CTF phosphorylation and that the 20 kD phospho-PS1 CTF band represents a less active or non-amyloidogenic form of γ-secretase.

Example 2

GSK-3α Regulates PS1-APP Association in SweAPP N2a Cells

Cell lysates of luteolin-treated SweAPP N2a cells were immunoprecipitated by PS1 antibody and probed for APP to clarify how phospho-PS1 CTF isoforms may regulate γ-secretase activity, seen in FIGS. 26(A) through 27(B). As illustrated in FIGS. 26(A) and (B), the APP-PS1 association is disrupted by luteolin, SB-415286 treatment, and GSK-3α siRNA. This treatment-mediated disruption has no correlation to full-length APP levels, as seen in FIGS. 27(A) and (B), indicating treatment has little effect on APP expression/trafficking. Thus, GSK-3α or, more specifically, downstream phosphorylation of the PS1 CTF plays an essential role in regulating the association of γ-secretase complex with its APP substrate.

Example 3

Luteolin Treatment Inhibits GSK-3 Activation and Results in Reduction of Cerebral Aβ Levels in Tg2576 Mice Eight month-old Tg2576 mice were treated with 20 mg/kg luteolin administered by daily intraperitoneal injection for 30 days to validate the above findings in vivo. Mice were anesthetized with isofluorane and transcardinally perfused with ice-cold physiological saline containing heparin (10 U/mL). Brains were rapidly isolated and quartered using a mouse brain slicer. The first and second anterior quarters were homogenized for Western blot analysis, and the third and fourth posterior quarters were used for microtome or cryostat sectioning. Brains were then fixed in 4% paraformaldehyde in PBS at 4° C. overnight and routinely processed in paraffin in a core facility at the Department of Pathology (USF College of Medicine). Five coronal sections from each brain (5-μm thickness) were cut with a 150-μm interval. Sections were routinely deparaffinized and hydrated in a graded series of ethanol prior to pre-blocking for 30 min at ambient temperature with serum-free protein block. GSK-3α/β immunohistochemical staining was performed using anti-phospho-GSK-3/α/β ($pTyr^{279/216}$) (Sigma, St. Louis, Mo.) antibody (1:50) in conjunction with the VectaStain Elite™ ABC kit coupled with diaminobenzidine substrate. Phospho-GSK-3α/β-positive neuronal cells were examined under brightfield using an Olympus BX-51 microscope.

Brain homogenates from these mice were subsequently analyzed by immunoprecipitation, Western blot, and ELISA, seen in FIGS. 28(A) through 37. As shown in FIGS. 28(A) and 28(B), both GSK-3α/β active isoforms from the homogenates of luteolin treated mice are reduced when compared to control. Moreover, ratios of each phosphorylated GSK-3 isoform to its respective holo protein revealed a significant decrease in activation with treatment (P<0.001). See FIGS. 28(a) and 28(B). These decreases in activation also appeared in the immunohistochemical analysis of GSK-3α/β activity in neurons of the CA1 region of the hippocampus and regions of the cingulate cortex. See FIGS. 30 through 33. Western blot analysis of PS1 from treated mice shows significantly lower levels of PS1 processing, comparing CTF to actin ratios (P<0.001). See FIGS. 29(A) and (C).

Brain homogenates were immunoprecipitated by PS1 antibody and probed for APP to confirm the proposed mechanism. Luteolin treatment effectively abolished PS1-APP association, seen in FIG. 34. Also, no significant changes in holo APP expression were observed following treatment and a potential decrease in oligomeric forms of Aβ even detected as illustrated in FIG. 35. To assess this decrease, ELISA was conducted on both soluble and insoluble $A\beta_{1-40, 42}$. See FIGS. 34 and 35. Luteolin treatment markedly reduced soluble isoforms of $A\beta_{1-40, 42}$ by 25% and 49%, respectively, depicted in FIG. 34, but no such reductions in insoluble Aβ isoforms were identified, seen in FIGS. 36 and 37.

GSK-3α inhibition has been shown to promote the phosphorylation of the CTF of PS1, whether achieved by pharmacological means or by genetic silencing. This phosphorylation subsequently disrupts the enzyme-substrate association with APP. During in vitro validation, significant increases in PS1 CTF phosphorylation (20 kD isoforms) was observed during luteolin, SB-415286, and GSK-3α RNAi treatment, which act with similar potency (luteolin and SB-415286) and efficacy. See FIGS. 24(A) through 25(B). Both in vitro and in vivo analysis reveal significant reductions in APP co-immunoprecipitated with PS1 following treatment, as seen in FIGS. 26(A) through 27(B) and 34 through 33. GSK-3α inhibition does not appear to phosphorylate full-length PS1 and does not affect endoproteolytic cleavage based on PS1 NTF analysis, as seen in FIGS. 23(A) and (B). Although phospho-PS1 CTFs was not detected in vivo, reductions in the 16 kD PS1 CTF bands, seen in FIGS. 29(A) through (C), were detected, which are indicative of a more highly active, amyloidogenic γ-secretase complex. Therefore, these compounds affect γ-secretase at the level of the CTF of PS1. There are some obvious complexities to the mechanism of dimerization of PS1 along with subsequent association with other essential γ-secretase components such as nicastrin, which recent studies suggest may function as the γ-secretase substrate receptor.

The presence of phosphorylated PS1 CTFs correspond with reduction of Aβ generation and accumulation of the β-CTF of APP, as was observed following luteolin treatment. See FIGS. 1 through 10(B). The accumulation β-CTFs following luteolin treatment is a fraction of β-CTF seen after direct γ-secretase inhibitor treatment (data not shown). In view of this finding, selective GSK-3 inactivation is a less toxic, more regulative, substrate-specific mode of γ-secretase inhibition. Earlier studies routinely employed phorbol-12,13-dibutyrate (PDBu), a potent PKC activator, as their phosphorylating agent. Thus, luteolin was tested for similar PKC activation, rather than a GSK-3 inhibitor. Co-treatment of SweAPP N2a cells with luteolin or SB-415286 and the PKC inhibitor GF109203X had no effect on GSK-3 inhibition (data not shown). Minor decreases in 20 kD and 18 kD phospho-PS1 CTF isoforms following GF109203X treatment, indicate PKC may play a part either in the downstream signaling mechanism or by directly phosphorylating the PS1 CTF. Additionally, there are no indications GSK-3α inhibition affects non-amyloidogenic processing of APP, since luteolin, SB-415286, and GSK-3α RNAi treatment have no effect on the maturation of TACE, ADAM10, or sAPPα release (data not shown), which are all strongly associated with PKC activation. This data indicates GSK-3α is an upstream regulator of PS1 CTF phosphorylation and consequently of γ-secretase activity.

Figure 13:
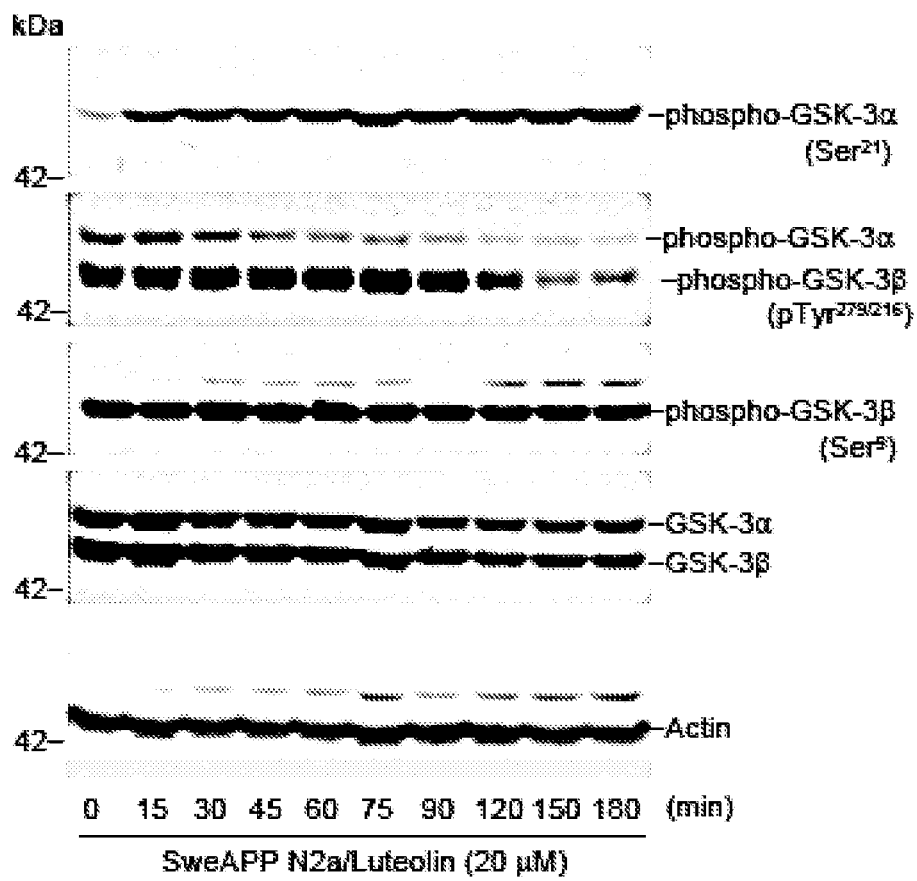
FIG. 13 is a blot showing luteolin selectively inactivates GSK-3α. SweAPP N2a cells were treated with luteolin at 20 μM for various time points as indicated. Cell lysates were prepared and subjected to Western blot analysis in phosphorylated forms of GSK-3α/β. Western blot analysis using anti-phospho-GSK-3α/β(Tye$^{279/216}$) antibody shows two bands (51 and 47 kDa) corresponding to phosphorylated forms of GSK-3α and GSK-3β or using anti-phospho-GSK-3β (Ser$^9$) antibody recognizes phosphorylated form of GSK-3β at 47 kDa. Anti-actin antibody was used as shows an internal reference control. Densitometry analysis shows the ratio of phospho-GSK-3α (Tye$^{279/216}$) to total GSK-3α as indicated below the figures (n=3 for each condition). A significant difference was noted between 30 min and 45, 60, 75, 90, 120, 150 or 180 min (P<0.005).
Figure 14:
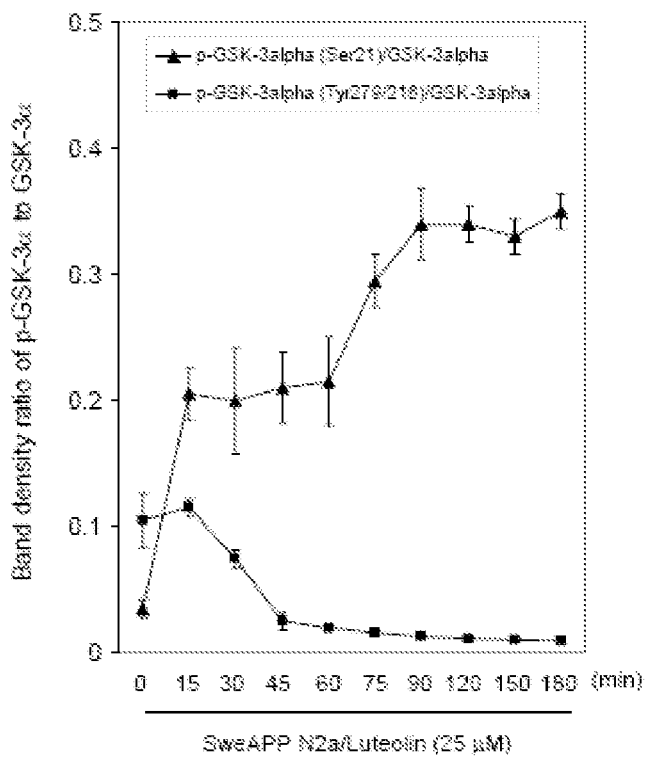
FIG. 14 is a graph showing luteolin selectively phosphorylates Serine 21 of GSK-3α. SweAPP N2a cells were treated with 20 μM luteolin for various time points as indicated. Cell lysates were prepared and subjected to Western blot analysis. Anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Western blot analysis using anti-actin antibody shows actin protein (as an internal reference control). Densitometry analysis shows the ratio of phospho-GSK-3α (Ser$^{21}$) to total GSK-3α as indicated below the figures (n=3 for each condition). One-way ANOVA followed by post hoc comparison revealed a significant difference between 0 min and 5, 10, 15, 20 or 25 min (P<0.001).
Figure 15:
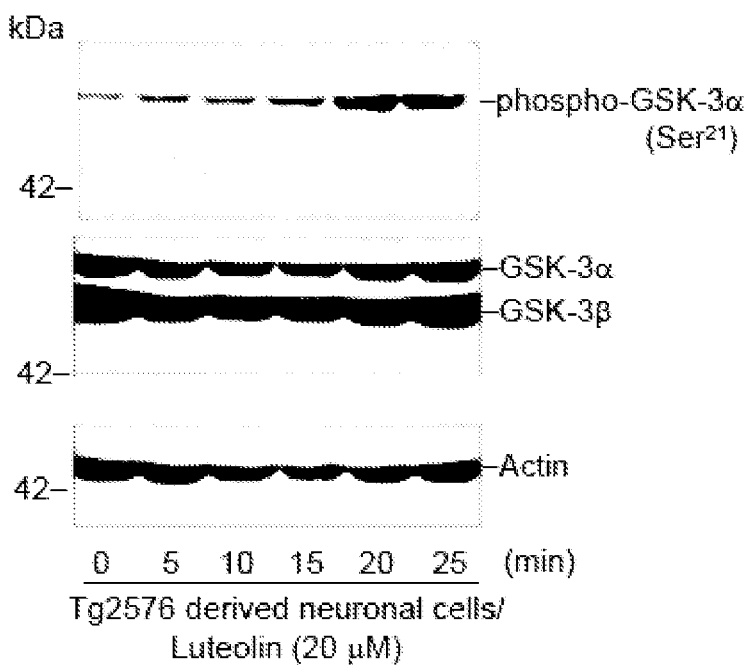
FIG. 15 is a blot showing luteolin selectively phosphohorylates Serine 21 of GSK-3α. Tg2576 derived neuronal cells were treated with 20 µM luteolin for various time points as indicated. Cell lysates were prepared and subjected to Western blot analysis in phosphorylated forms of GSK-3α/β. Western blot analysis using anti-phospho-GSK-3α/β (Tye$^{279/216}$) antibody shows two bands (51 and 47 kDa) corresponding to phosphorylated forms of GSK-3α and GSK-3β or using anti-phospho-GSK-3β (Ser$^9$) antibody recognizes phosphorylated form of GSK-3β at 47 kDa. Anti-actin antibody was used as shows an internal reference control.
Figure 16:
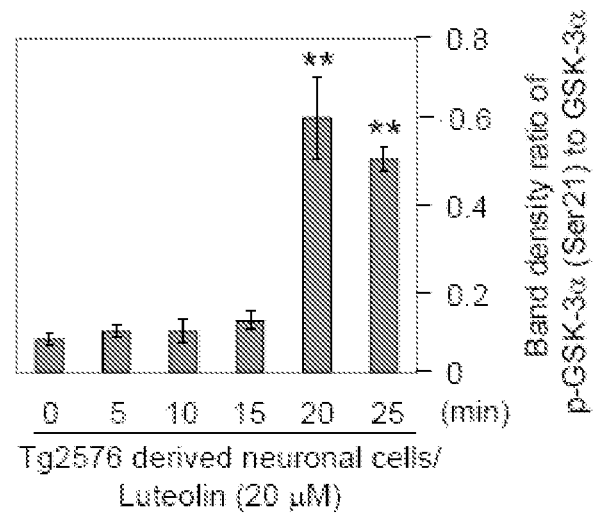
FIG. 16 is a graph of the blot in FIG. 15, and showing luteolin selectively phosphohorylates Serine 21 of GSK-3α. Densitometry analysis shows the ratio of phospho-GSK-3α (Tye$^{279/216}$) to total GSK-3α as indicated below the figures (n=3 for each condition). A significant difference was noted between 30 min and 45, 60, 75, 90, 120, 150 or 180 min (P<0.005).
Figure 17:
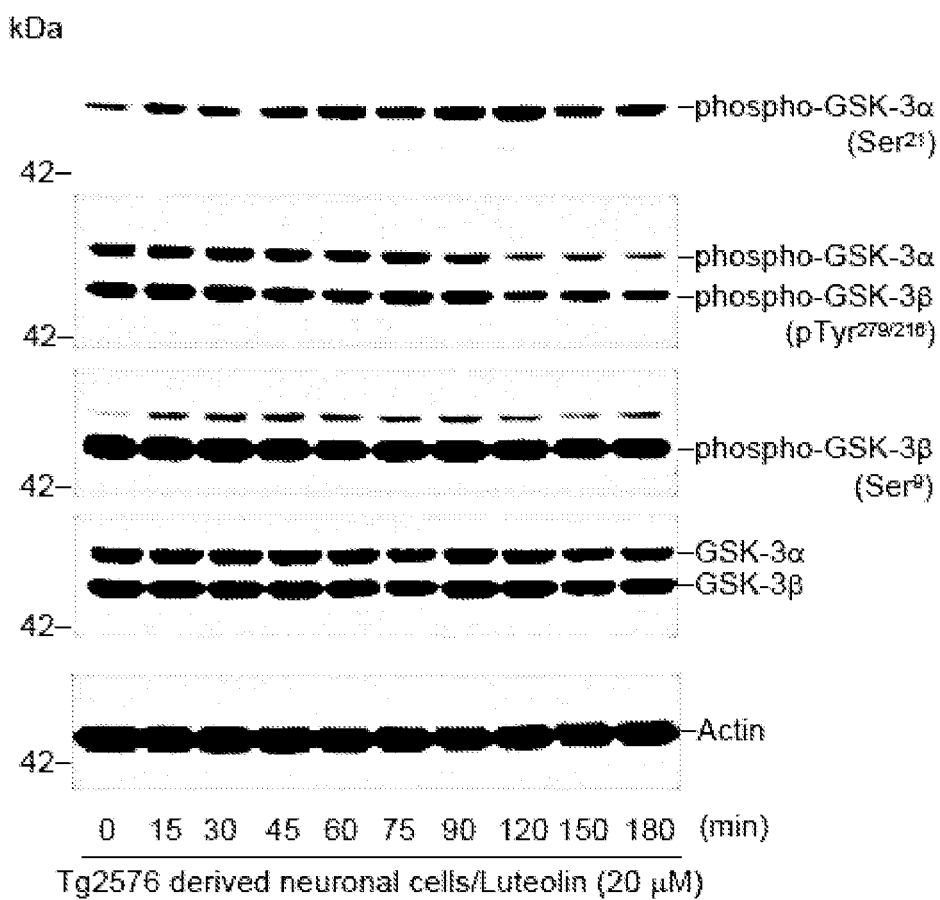
FIG. 17 is a blot indicating luteolin selectively inactivates GSK-3α. Tg2576 derived neuronal cells were treated with luteolin at 20 µM for various time points as indicated. Cell lysates were prepared and subjected to Western blot analysis in phosphorylated forms of GSK-3α/β. Western blot analysis using anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Anti-phospho-GSK-3α/β(Tye$^{279/216}$) antibody shows two bands (51 and 47 kDa) corresponding to phosphorylated forms of GSK-3α and GSK-3β or using anti-phospho-GSK-3β (Ser$^9$) antibody recognizes phosphorylated form of GSK-3β at 47 kDa. Anti-actin antibody was used as an internal reference control.
Figure 18:
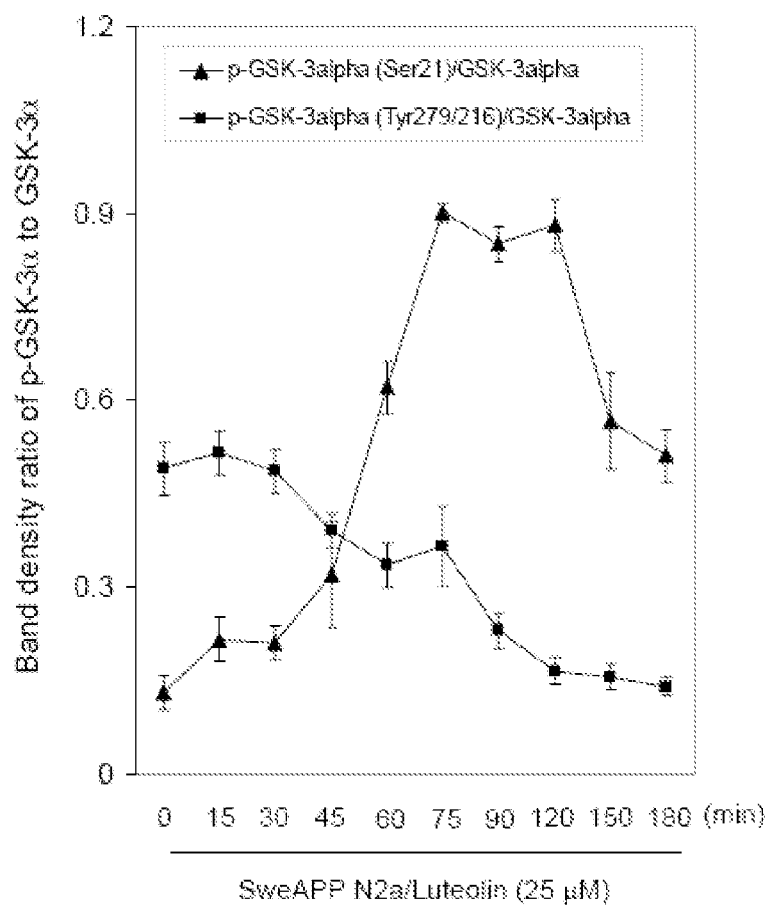
FIG. 18 is a graph of the protein levels of GSK-3α and GSK-3β following luteolin treatment. SweApp N2a cells were treated with 25 µM luteolin for the times indicated. Cell lysates were prepared and subjected to Western blot, probing for anti-phospho-GSK-3α (Ser$^{21}$) and phospho-GSK-3α (Tye$^{279/216}$). Densitometry analysis was conducted of the ratio of phospho-GSK-3α (Ser$^{21}$) to total GSK-3α or phospho-GSK-3α (Tye$^{279/216}$) to total GSK-3α (n=3 for each condition). One-way ANOVA followed by post hoc comparison revealed a significant difference between 30 min and 45, 60, 75, 90, 120, 150 or 180 min (P<0.005).
Figure 19:
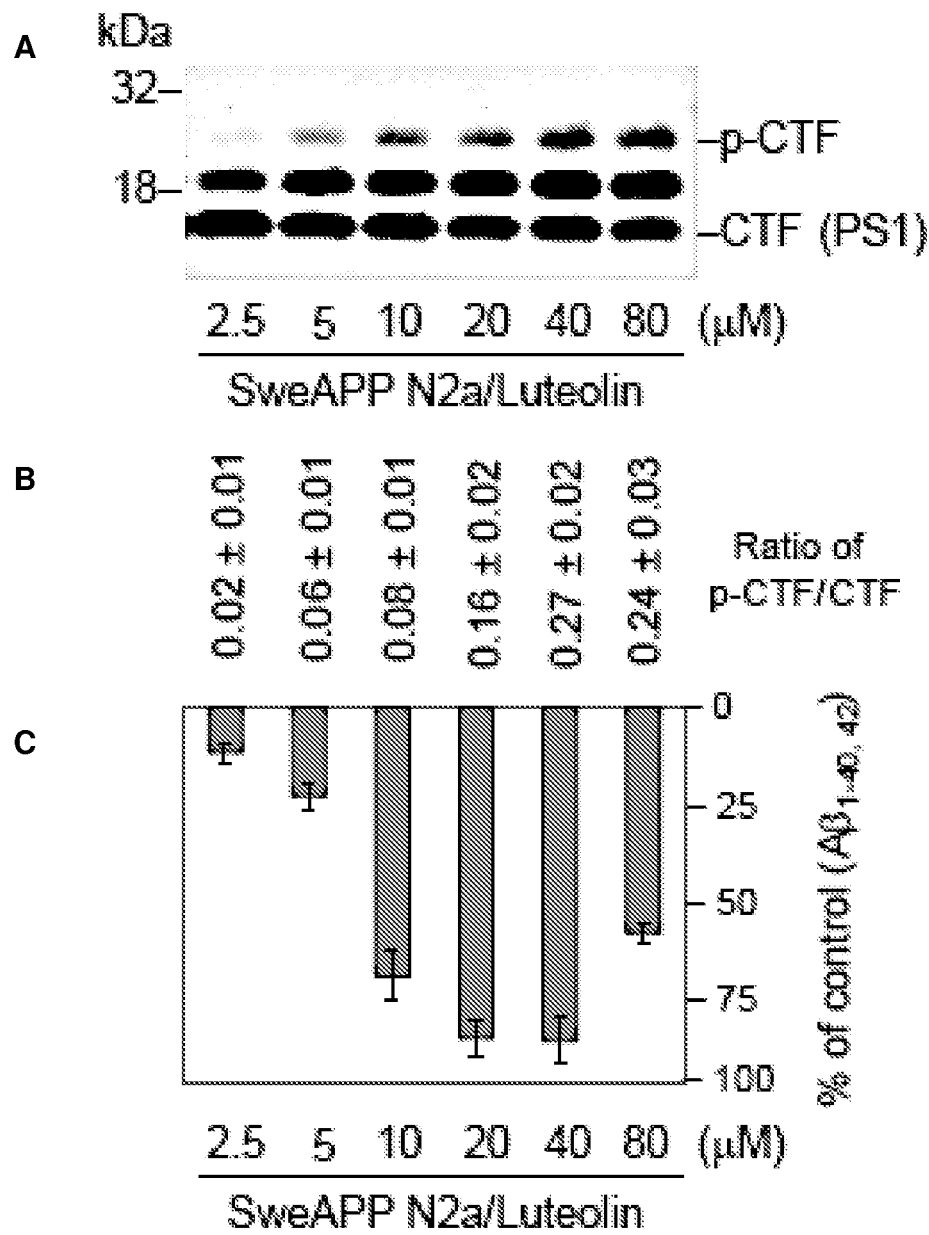
FIG. 19 is a blot showing PS1 phosphorylation is associated with luteolin-mediated inhibition of Aβ generation. SweAPP N2a cells were treated with luteolin at indicated doses for 4 hrs. Cell lysates were prepared from these cells and subjected to Western blot analyses of PS1 C-terminal fragments (CTF). (A) Western blot analysis by anti-PS1 CTF antibody shows two bands corresponding to phosphorylated PS1 CTF (p-CTF) and one dephosphorylated PS1 CTF (CTF). (B) Densitometry analysis shows the ratio of PS1 p-CTF to CTF. At test revealed a significant deference between luteolin doses and time points for ratio of PS1 p-CTF to CTF (P<0.005 with n=3 for each condition, but not for ratio of holo PS1 to PS1 NTF (P>0.05 with n=3 for each condition) at each time-point examined. (C) Cultured media were collected for Aβ ELISA. Data corresponds to percentage of Aβ$_{1-40, 42}$ peptides secreted 4 hrs after luteolin treatment relative to control (untreated) as indicated.
Figure 20:
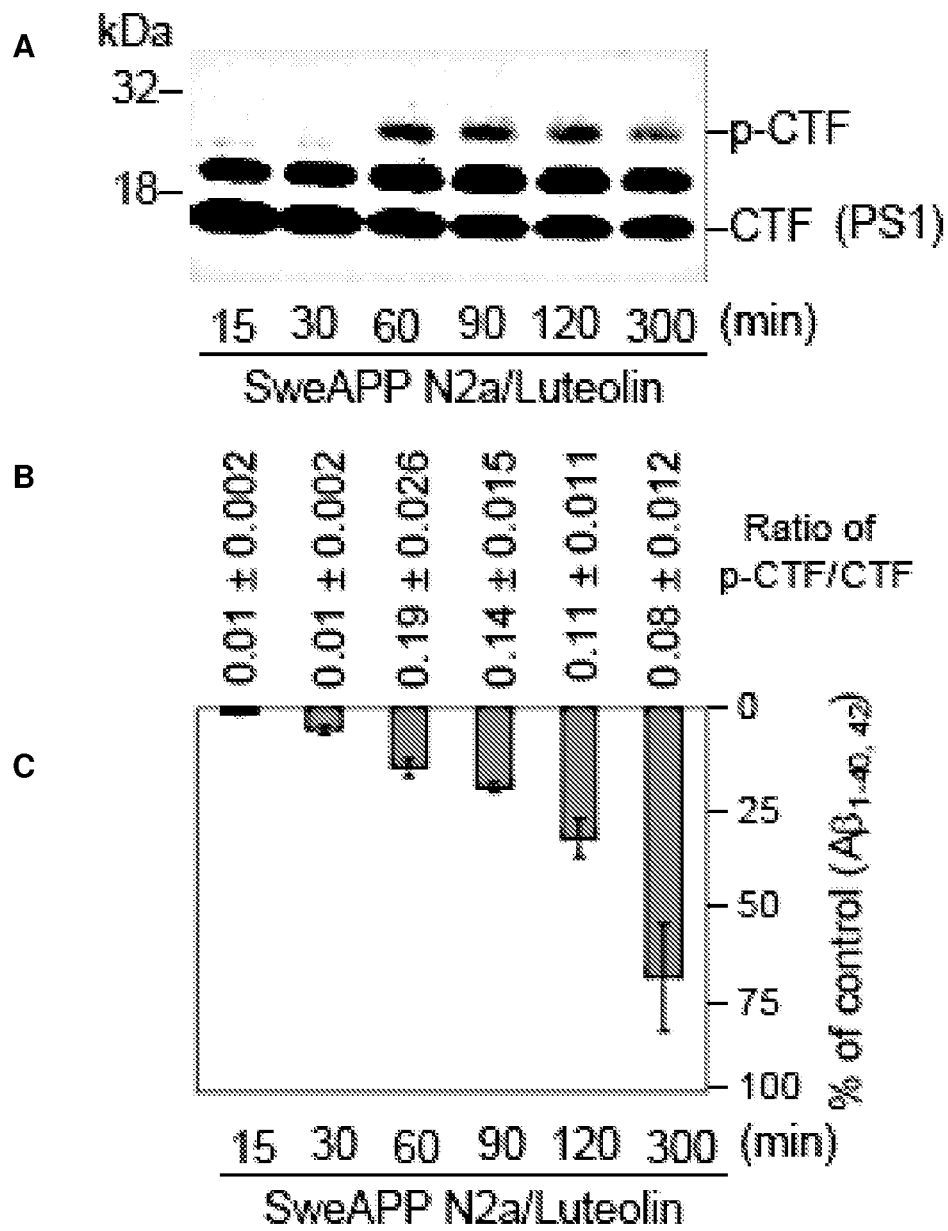
FIG. 20 shows PS1 phosphorylation is associated with luteolin-mediated inhibition of Aβ generation. SweAPP N2a cells were treated with luteolin at 20 µM for various time points as indicated. Cell lysates were prepared from these cells and subjected to Western blot analyses of PS1 C-terminal fragments (CTF). (A) Western blot analysis by anti-PS1 CTF antibody shows two bands corresponding to phosphorylated PS1 CTF (p-CTF) and one dephosphorylated PS1 CTF (CTF). (B) Densitometry analysis shows the ratio of PS1 p-CTF to CTF. At test revealed a significant deference between luteolin doses and time points for ratio of PS1 p-CTF to CTF (P<0.005 with n=3 for each condition, but not for ratio of holo PS1 to PS1 NTF (P>0.05 with n=3 for each condition) at each time-point examined. (C) Cultured media were collected for Aβ ELISA. Data corresponds to percentage of Aβ$_{1-40, 42}$ peptides secreted 4 hrs after luteolin treatment relative to control (untreated) as indicated.
Figure 21:
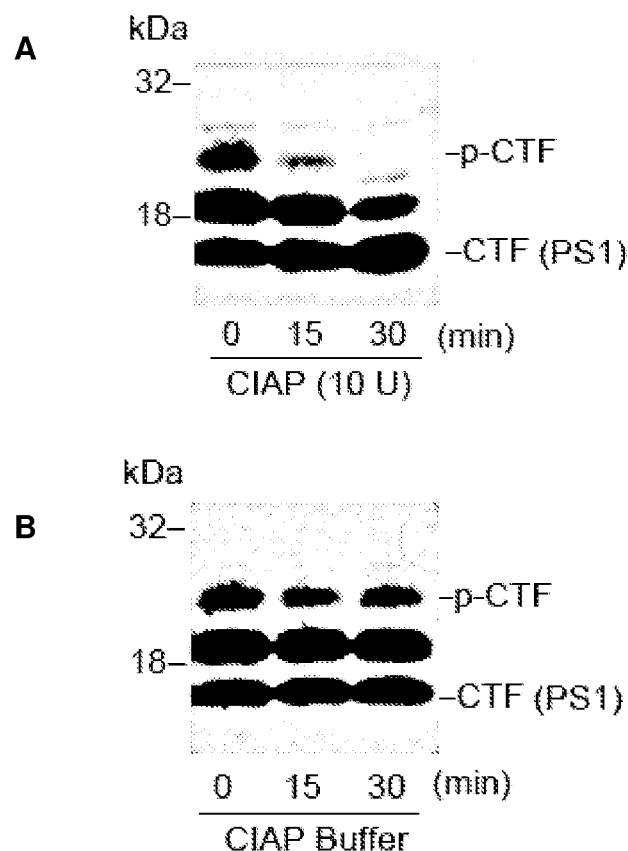
FIG. 21 is a blot depicting PS1 phosphorylation is associated with luteolin-mediated inhibition of Aβ generation. SweAPP N2a cells were treated with luteolin (20 µM) for 30 min During the luteolin incubation, cell lysates were incubated with (A) calf-intestine alkaline phosphatase (CIAP) for 30 min or (B) buffer for various time points. Western blot analysis by anti-PS1 CTF antibody confirms two higher molecular weight bands corresponding to phosphorylated isoforms.
Figure 22:
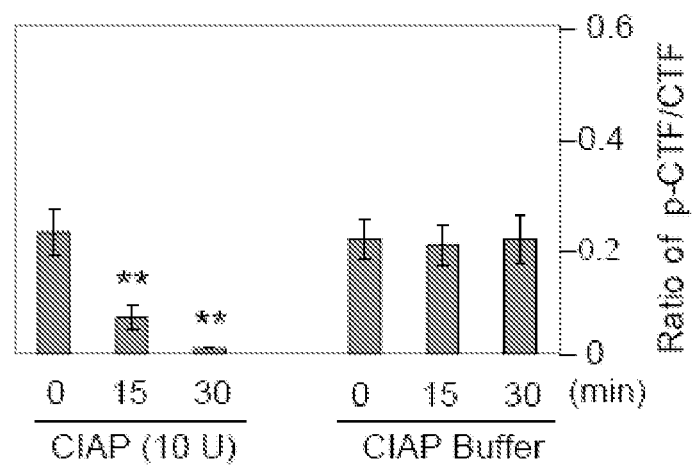
FIG. 22 is a densitometric graph of the blots in FIG. 21, showing the ratio of PS1 p-CTF to CTF.
Figure 23:
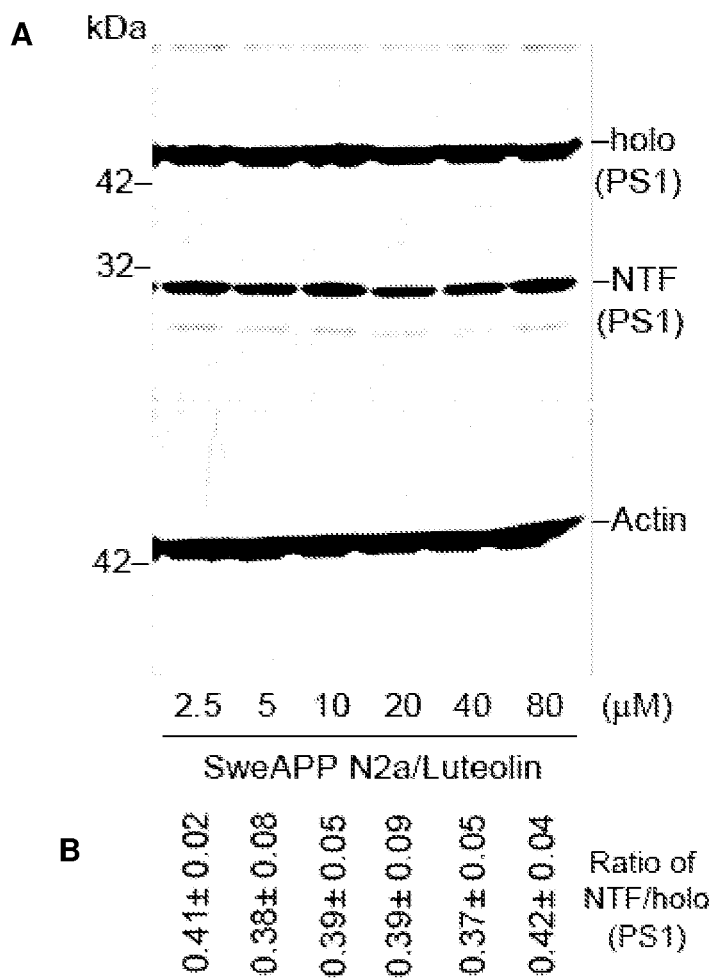
FIG. 23 shows PS1 phosphorylation is associated with luteolin-mediated inhibition of Aβ generation. SweAPP N2a cells were treated with luteolin at a range of doses for 4 hrs. Cell lysates were prepared from these cells and subjected to Western blot analyses of PS1 N-terminal fragment (NTF). Western blot analysis by anti-PS1 CTF antibody shows two bands corresponding to phosphorylated PS1 CTF (p-CTF) and one dephosphorylated PS1 CTF (CTF). (B) At test of the densitometry analysis revealed a significant deference between luteolin doses and time points for ratio of PS1 p-CTF to CTF (P<0.005 with n=3 for each condition) of FIGS. 19(C) and 20(C), but not for ratio of holo PS1 to PS1 NTF (P>0.05 with n=3 for each condition) at each time-point examined.

Luteolin selectively inactivates GSK-3α isoforms over β isoforms, shown in FIGS. 11 through 18, as luteolin does not inhibit active GSK-3β isoforms at about 2 hrs, depicted in FIGS. 13 and 17, compared to control (data not shown). However, active GSK-3α isoforms are more timely and effectively reduced by luteolin treatment, depicted in FIGS. 13 and 17, indicating luteolin differs from other GSK-3 inhibitors due to its selectivity (including SB-415286). β-catenin also remains unaffected by luteolin treatment, which may imply that this selective GSK-3 inhibition can circumvent the potential toxicity of more general GSK-3 inhibitors (data not shown). Furthermore, there is a clear correlation between increases in inactive and decreases in active GSK-3α, seen in FIGS. 14 and 18, following treatment, shows that luteolin affects the positive feedback loop of GSK-3 activation by inactivating the PP1 phosphatase.

Figure 24:
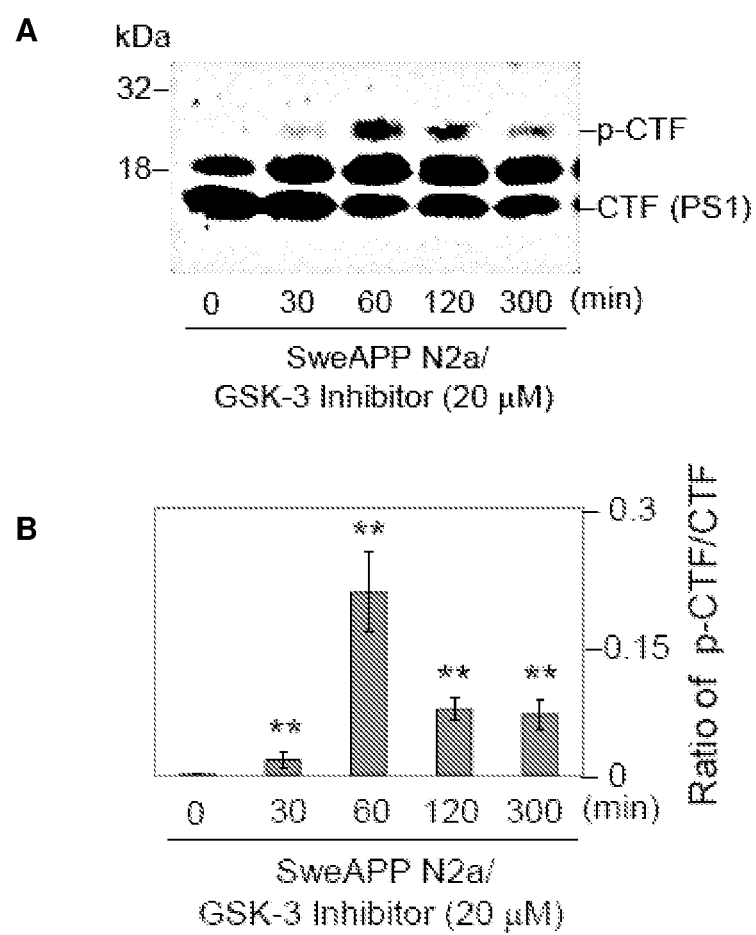
FIG. 24 depicts GSK-3α regulating PS1 phosphorylation. SweAPP N2a cells were treated with a known GSK-3 inhibitor (SB-415286) at 20 µM for various time points. (A) Western blot analysis by anti-PS1 CTF antibody produces consistent PS1-CTF levels among non-treated and luteolin treated cells, whereas PS1-CTF phosphorylation profiles increase sharply at 60 minutes but quickly stabilize at a lower, though elevated, level. (B) Densitometry analysis shows the ratio of PS1 p-CTF to CTF and ratio of holo PS1 to actin as indicated. At test revealed significant differences between time points for the ratio of PS1 p-CTF to CTF (P<0.001 with n=3 for each condition).
Figure 25:
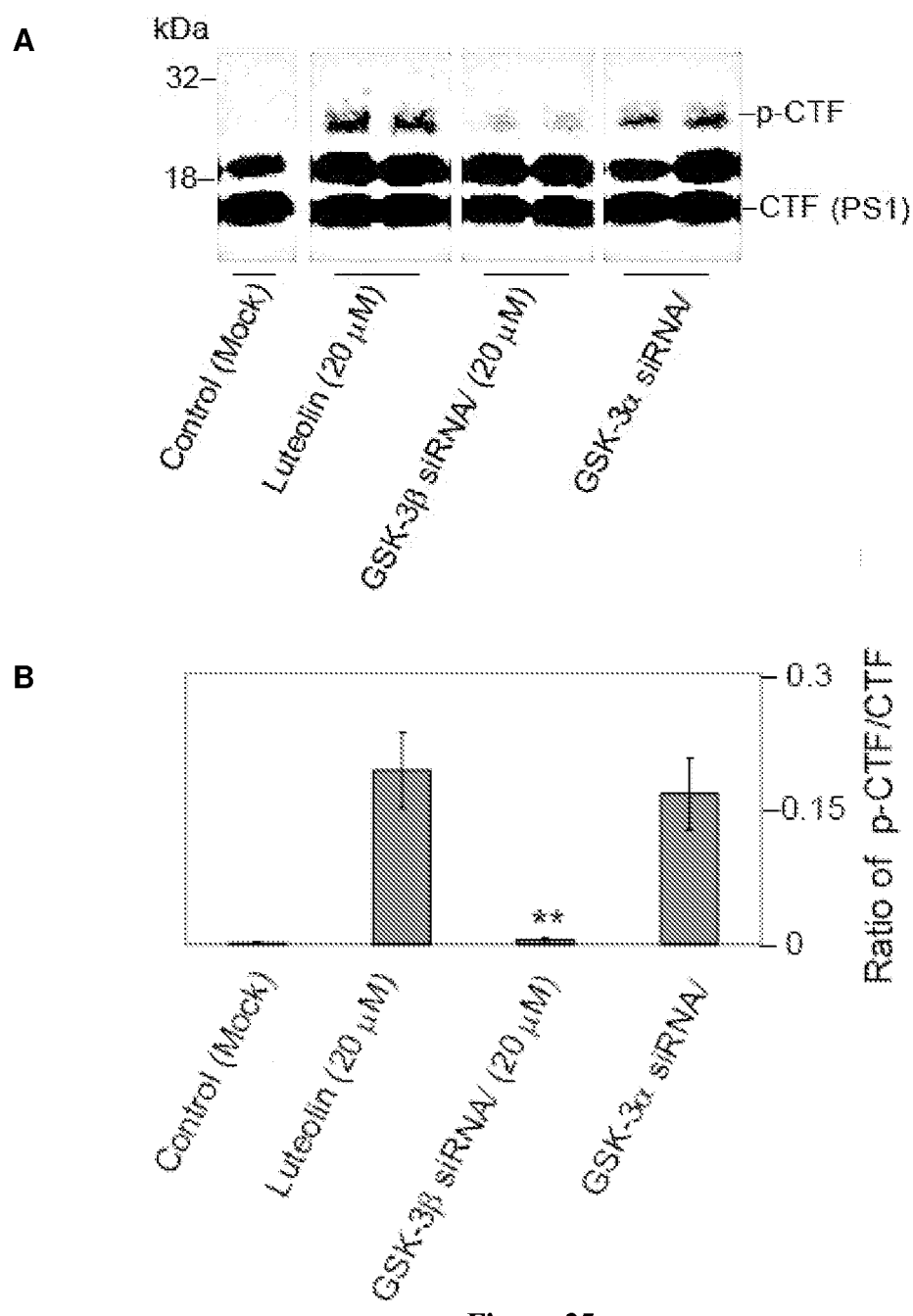
FIG. 25 depicts GSK-3α regulating PS1 phosphorylation. SweAPP N2a cells transfected with siRNA targeting GSK-3α, β, or mock transfected 48 hrs post-transfection. Prior to experiments, siRNA knockdown efficiency >70% for GSK-3α, β was confirmed by Western blot analysis (data not shown). (A) The expression of PS1 C-terminal fragments was analyzed by Western blot in cell lysates of the transfected cells. (B) Densitometric analysis reveals the ratio of PS1 p-CTF to CTF as indicated. At test revealed significant differences between GSK-3α siRNA-transfected cells and GSK-3β siRNA or control (Mock transfected cells) (P<0.001 with n=4 for each condition) on the ratio of PS1 p-CTF to CTF. In addition, at test also revealed significant differences between luteolin treated cells and GSK-3β siRNA or control (Mock transfeced cells) (P<0.001 with n=4 for each condition) on the ratio of PS1 p-CTF to CTF.

Luteolin treatment markedly reduces both soluble $A\beta_{1-40, 42}$ isoforms in vivo, seen in FIGS. 24 and 35, illustrating the anti-amyloidogenic agent-effect of luteoline. No changes in insoluble $A\beta_{1-40, 42}$ isoforms were observed, seen in FIGS. 24 and 35, however this result is expected given the age and consequent low plaque burden of these Tg2576 mice. Luteolin potentially reaches its molecular target by passive diffusion through cell membranes, explaining the rapid onset of GSK-3α inhibition observed following luteolin treatment, depicted in FIGS. 11, 12, 15, and 16, and may indicate favorable blood-brain barrier permeability. See FIGS. 26(A) through 35.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating Alzheimer's disease comprising:
  administering a therapeutically effective amount of lutoelin to a patient suffering from Alzheimer's disease;
  wherein the luteolin is administered at a dosage of 20 mg/kg of body weight.

2. A method of treating Alzheimer's disease comprising:
  administering an effective amount of lutoelin to a patient suffering from Alzheimer's disease;
  wherein the luteolin is administered at a plasma concentration of 20 µM, 40 µM, or at a range of between 2.5 µM to 80 µM.

3. A method of treating Alzheimer's disease comprising:
  administering a therapeutically effective amount of a GSK-3 inhibitor to a patient suffering from Alzheimer's disease, wherein the GSK-3 inhibitor is selected from the group consisting of GSK-3β siRNA, and lutoelin;
  a range of between 2.5 µM to 80 µM, or at a dosage of 20 mg/kg body weight.

4. A method of treating Alzheimer's disease comprising:
  inactivating glycogen synthase kinase 3 alpha (GSK-3α) activity by administering a therapeutically effective amount of lutoelin to a patient suffering from Alzheimer's disease;
  wherein the flavonoid compound is administered at a plasma concentration of 20 µM, 40 µM, at a range of between 2.5 µM to 80 µM, or at a dosage of 20 mg/kg of body weight.

* * * * *